United States Patent [19]
Wilson et al.

[11] Patent Number: 6,133,416
[45] Date of Patent: Oct. 17, 2000

[54] INHIBITION OF CELL GROWTH BY AN ANTI-PROLIFERATIVE FACTOR

[75] Inventors: Deborah R. Wilson, Houston; Mary Lapadat-Tapolsky, The Woodlands; Therese M. Timmons, Houston; Julia A. Lee, Houston; Brian D. Almond, Houston; Jack A. Roth, Houston, all of Tex.

[73] Assignee: The University of Texas System Board of Regents, Austin, Tex.

[21] Appl. No.: 08/918,712

[22] Filed: Aug. 22, 1997

Related U.S. Application Data

[60] Provisional application No. 60/024,343, Aug. 23, 1996.
[51] Int. Cl.[7] .............................. C07K 2/00; C07K 4/00; C07K 5/00; A61K 45/00
[52] U.S. Cl. ......................... 530/300; 424/283.1; 436/63
[58] Field of Search ............................... 435/7.23; 514/2; 424/283.1; 436/63, 64; 530/300

[56] References Cited

U.S. PATENT DOCUMENTS 5,523,290  6/1996  Le Boeuf et al. ......................... 514/21

FOREIGN PATENT DOCUMENTS

| 0 325 471 | 7/1989 | European Pat. Off. . |
| 0 353 772 | 2/1990 | European Pat. Off. . |
| WO 95/12660 | 5/1995 | WIPO . |
| WO 95/24208 | 9/1995 | WIPO . |
| WO 96/09060 | 3/1996 | WIPO . |

OTHER PUBLICATIONS

Tsuji et al. "Production of a low molecular weight growth inhibitory factor by adenovirus 12–transformed cells" Bichemical and Biophysical Research Communications. vol. 187. No. 3, pp. 1232–1240, Sep. 30, 1992.
Belani, "Multimodality management of regionally advanced non–small–cell lung cancer," *Sem. Oncol.,* 20(4):302–314, 1993.
Bouck, "P53 and angiogenesis," *Biochim. Biophys. Acta,* 1287:63–66, 1996.
Culver et al., "Gene therapy for solid tumors," *British Med. Bull.,* 51(1):192–204, 1995.
Goyette et al., "Progression of colorectal cancer is associated with multiple tumor suppressor gene defects but inhibition of tumorigenicity is accomplished by correction of any single defect via chromosome transfer," *Mol. Cell Biol.,* 12(3):1387–1395, 1992.
Gruentzig et al., "Long–term follow up after PTCA: the early Zurich experience," *N. Engl. J. Med.,* 316:1127–1132, 1987.
Hannun and Bell, "The sphingomyelin cycle and the second messenger function of ceramide," *J. Biol. Chem.,* 269(5):3125–3128, 1994.
Hannun and Bell, "Functions of sphingolipids and sphingolipid breakdown products in cellular regulation," *Science,* 243:500–507, 1989.
Klein et al., "High–velocity microprojectiles for delivering nucleic acids into living cells," *Nature,* 327:70–73, 1987.
Leimgruber et al., "Restenosis after successful coronary angioplasty in patients with single vessel disease," *Circulation,* 73:710–717, 1986.
Montenarh, "Biochemical, immunological, and functional aspects of the growth–suppressor/oncoprotein p53," *Crit. Rev. Oncogen.,* 3:233–256, 1992.
Nobuyoshi et al., "Restenosis after successful percutaneous transluminal coronary angioplasty: serial angiographic follow–up of 220 patients," *J. Am. Coll. Cardiol.,* 12:616–623, 1988.
Roth et al., "Gene replacement strategies for the prevention and therapy of cancer," *Eur. J. Cancer,* 30A:2032–2037, 1994.
Serruys et al., "Incidence of restenosis after successful coronary angioplasty: a time–related phenomenon. A quantitative angiographic study in 342 consecutive patients at 1, 2, 3, and 4 months," *Circulation,* 77:361–371, 1988.
Van Meir et al., "Release of an inhibitor of angiogenesis upon induction of wild type p53 expression in glioblastoma cells," *Nature Genetics,* 8:171–176, 1994.
Verheij et al., "Requirements for ceramide–initiated SAPK/JNK signalling in stress–induced apoptosis," *Nature,* 380:75–79, 1996.
Wong et al., "Appearance of b–lactamase activity in animal cells upon liposome mediated gene transfer," *Gene,* 10:87–94, 1980.
Watanabe et al., "Recombinant Human Betacellulin," *J. Biol. Chem.,* 269(13):9966–9973, 1994.
Carbone et al., "Biochemical Properties of Media Conditioned by Simian Virus 40–induced Hamster Tumor Cells: Correlation with Distinct Cell Phenotypes but not with Oncogenicity," *Cancer Research,* 49:6809–6812, 1989.
International Search Report, Jan. 20, 1998 (INGN:026P).

*Primary Examiner*—Yvonne Eyler
*Attorney, Agent, or Firm*—Fulbright & Jaworski

[57] ABSTRACT

The present invention involves the identification of a factor or factors that are anti-proliferative and can be used in the treatment of cancers and other hyperproliferative disease states. The factor or factors are induced from cells follow contact of the cells with viral or plasmid expression vectors. One factor is between about 3 kDa and 300 kDa in size, while another is less than about 3 kDa in size. Both are heat stable and is resistant to both protease and nuclease treatment. Methods for purification and use of the factor also are disclosed.

15 Claims, 10 Drawing Sheets

INHIBITION OF CELL GROWTH BY AN ANTI-PROLIFERATIVE FACTOR

This application claims priority on provisional application U.S. Ser. No. 60/024,343, filed Aug. 23, 1996.

BACKGROUND OF THE INVENTION

1. Field of the Invention

The present invention relates generally to the field of cancer and hyperproliferative cell therapy. More particularly, it concerns a methods for inhibiting the growth and/or killing of cells by contacting cells with a cytotoxic/cytostatic agent.

2. Description of Related Art

Normal tissue homeostasis is achieved by an intricate balance between the rate of cell proliferation and cell death. Disruption of this balance either by increasing the rate of cell proliferation or decreasing the rate of cell death can result in the abnormal growth of cells and is thought to be a major event in the development of cancer, as well as other cell proliferative disorders such as restenosis.

The effects of cancer are catastrophic, causing over half a million deaths per year in the United States alone. Conventional strategies for the treatment of cancer include chemotherapy, radiotherapy, surgery or combinations thereof, however further advances in these strategies are limited by lack of specificity and excessive toxicity to normal tissues. In addition, certain cancers are refractory to treatments such as chemotherapy, and some of these strategies such as surgery are not always viable alternatives. For example, non-small-cell lung cancer (NSCLC), which includes squamous cell carcinoma, adenocarcinoma and large-cell carcinoma, accounts for 75–80% of all lung cancers (American Cancer Society, 1993). Current multimodality therapeutic strategies applied to regionally advanced NSCLC are minimally effective with the overall cure rate being only about 10% (Belani, 1993; Roth et al., 1994).

Cancer is now understood to be the result of multiple genetic changes (Goyette et al., 1992; Klein et al., 1987) and it is well established that many cancers are caused, at least in part, by genetic alterations that result in either the over expression of one or more genes, or the expression of abnormal or mutant gene or genes. For example, the expression of oncogenes is known to play a role in the development of cancer. Oncogenes are defined as genetically altered genes whose mutated expression product somehow disrupts normal cellular function or control (Spandidos et al., 1989). These types of mutations are believed to have effects on the malignant growth of cells derived from practically every tissue.

Another type of gene of interest in the development of cancer is the tumor suppressor gene. Mutations in these genes result in loss of function of the normal cellular gene product, which are involved in the suppression of the neoplastic phenotype. The p53 gene is well recognized as a tumor suppressor gene (Montenarh, 1992). There is considerable evidence linking mutations in p53 in the oncogenesis of many human cancers. There are many reports demonstrating that the neoplastic growth of colon, glioblastoma, breast, osteosarcoma, and lung tumor cells can be suppressed by the expression of wild-type p53. For example, the introduction of wild-type p53 into a variety of cell types or tumors with p53 mutations or deletions, using viral delivery methods, has resulted in the expression of the wild-type p53 transgene and a suppression of the malignant phenotype. Furthermore, introduction of wild type 53 into certain types of p53 wild type tumor cells suppresses their growth. These types of observations demonstrate that high levels of expression of wild-type p53 are a desirable effect for the treatment of p53-dependent oncogenic malignancies.

Other types of hyper-proliferative disorders have also been the target of gene therapy. Restenosis, characterized by the regrowth of smooth muscle cells into the lumen of blood vessels following angioplasty or other arterial damage, is a frequent and recurring problem in the long term success of angioplasty. The failure rates of angioplasty as a result of restenosis within six months are reported to be between 25–50% (Leimgruber et al., 1986; Gruentzieg et al., 1987; Nobuyoshi et al., 1988; Serruys et al., 1988). Restenosis also occurs after arterial reconstructions, atherectomy, stent implantation, and laser angioplasty. Injury to arteries during angioplasty results in the activation of medial smooth muscle cells, which begin to migrate and proliferate into the lumen of the artery to form a neointima, or a new layer of cells. It is believed that expansion of this neointima as a result of the new layer of smooth muscle cells, extracellular matrix, and recruited inflammatory cells, is the cause of the eventual reduction of blood flow through the artery and recurrence of ischemic symptoms. Currently it is believed that the administration of gene therapy constructs encoding the HSV-thymidine kinase or cytosine deaminase gene may be beneficial to prevent restenosis. Similarly, it is envisioned that gene therapy may be useful for the treatment of other hyper-proliferative cellular disorders including psoriasis and rheumatoid arthritis.

Generally, both standard chemo- and radiotherapies, as well as transfer of genetic material into cells, have limitations; there clearly remains a need for improved strategies of anti-cancer and anti-proliferative cell therapy. In particular there is a need to increase the level of growth inhibition beyond that induced by traditional gene therapy modalities.

SUMMARY OF THE INVENTION

It is, therefore, a goal of the present invention to provide improved methods and compositions for the treatment of cancer and other hyperproliferative cellular disorders. More particularly, it is a goal to provide methods for producing a factor or factors that exhibit(s) anti-proliferative activity against cells, and compositions for this kind of therapy. These methods and compositions can work alone or potentiate the effects of radiotherapy, chemotherapy or gene therapy through the provision of, or induction of, a cytotoxic/cytostatic, anti-proliferative factor.

Therefore, in accordance with the present invention, there is provided a purified anti-proliferative factor produced by a process comprising the steps of (a) contacting a cell with a transcriptionally active expression vector; (b) culturing said cell in cell culture media; and (c) purifying said anti-proliferative factor. The process may further comprise the step of removing said cell from said cell culture media.

In another embodiment, there is provided a method for purifying an anti-proliferative factor comprising the steps of (a) contacting a cell with a transcriptionally active expression vector; (b) culturing said cell in cell culture media; and (c) purifying said anti-proliferative factor. The process may further comprise the step of removing said cell from said cell culture media In yet another embodiment, there is provided an anti-proliferative factor having the following characteristics: (a) resistant to protease; (b) resistant to nuclease; (c) resistant to high heat; (d) resistant to freezing-thaw; (e) resistant to lyophilization; (f) pH stable; and (g) has an apparent molecular weight of less than about 3 kDa or less than about 300 kDa.

In still yet another embodiment, there is provided a method of inhibiting the growth of a cell comprising the step of contacting said cell with an anti-proliferative factor produced in accordance with the methods above.

In still yet a further embodiment, there is provided a method of treating a hyper-proliferative disease comprising the step of contacting a cell lacking normal cell growth regulation with an anti-proliferative factor produced in accordance with the methods above.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
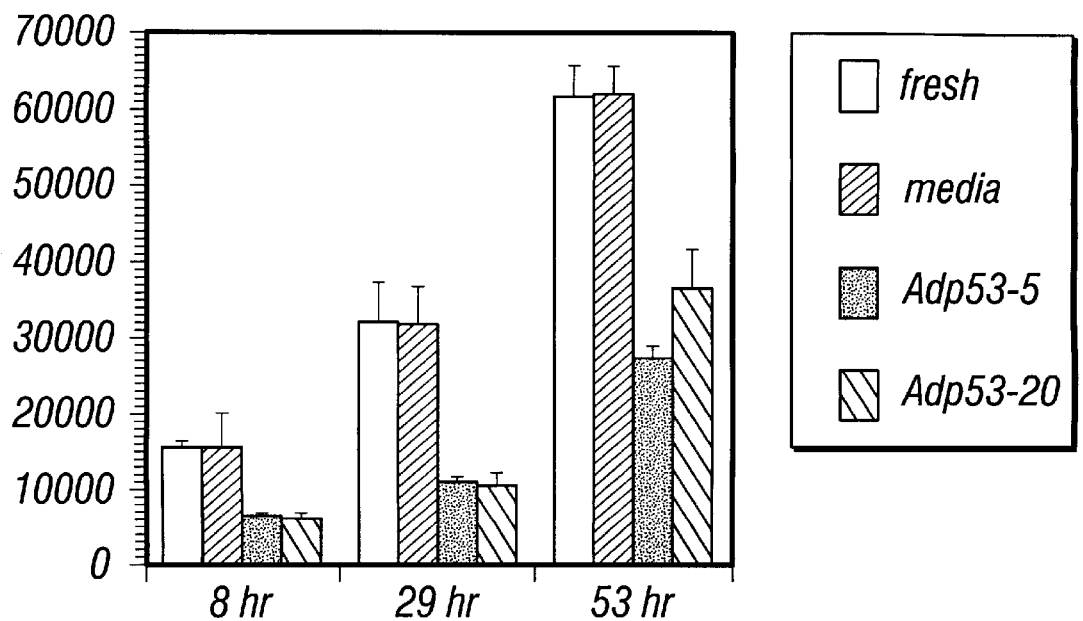
FIG. 1—Growth inhibition of naïve H1299 cells after treatment with supernatant from Adp53-infected H1299 cells. Naïve H1299 cells were seeded in 96 well plates at a confluency of approximately 19% and fresh media ($1^{st}$ bar from left in each set), supernatant from uninfected H1299 cells ($2^{nd}$ bar), Adp53-infected H1299 cells at an multiplicity of infection (MOI) of 5 ($3^{rd}$ bar), or Adp53-infected H1299 cells at an MOI of 20 ($4^{th}$ bar), was added to each well. Cell growth was measured as $^3$H-thymidine incorporation at 8, 29 and 53 hours.

Cancer accounts for the death of over half a million people each year in the United States alone. The causes of cancer are multifactorial, but it is known that aberrations in mechanisms controlling cell death as well as up-regulated expression of certain genes may result in increased proliferation of cells, and hence the development of the neoplastic state. Conventional strategies for the treatment of cancer include radiotherapy, chemotherapy and surgery; however, these treatment modalities are limited and are not effective on some tumors. More recently it has been observed that the targeting of specific genetic lesions may allow for the selective destruction of tumor cells while limiting the effects of toxicity often associated with chemotherapy or radiotherapy. These new therapies include the suppression of activated oncogenes that drive proliferation of a tumor cell as well as the restoration of the normal activity of mutated tumor suppressor genes. Gene therapy still suffers from various limitations, and methods to improve the efficacy of gene therapy, as well as the efficacy of more standard therapeutic regimens, is needed.

The present invention provides a novel approach to cancer therapy as well as a means of increasing the effectiveness of existing cancer therapies. The present invention relies, in part, on the observation that tumor cells manipulated in a particular fashion produce a factor, found in the cell medium, that exhibits an anti-proliferative effects on neighboring cells. This factor has been partially purified and characterized.

The factor may be employed in a number of ways. First, the factor may be utilized by itself in a therapeutic regimen by administering the isolated factor to tumors or other hyper-proliferative cells. Second, utilization of certain protocols will induce the factor, such as treatment of cells with a viral or plasmid vector; it is envisioned that the vectors also will encode a therapeutic gene that can have additional anti-proliferati effects on treated cells. Third, the factor may be utilized in combination with standard chemo- and radiotherapy, by administering the factor to a tumor or other hyper-proliferative cell prior to, at the same time as, or following a standard chemo- or radiotherapy. Fourth, it is possible to combine the factor, gene therapy and standard chemo- or radiotherapy in a single patient.

As described in greater detail below, the factor has been identified in the cell medium of cells treated with various viral and plasmid vectors, where the vectors express various exogenous polypeptides. The term treated refers to placing in close proximity (i) a target cell and (ii) the vector, such that the cell will "take up" or internalize the vector and express the gene product for which it codes. The molecular weight of one factor is less than about 3 kDa, while a second is less than about 300 kDa. The factor further is characterized by its ability to inhibit the growth in cells to which it is administered.

In the context of the current invention, the likely targets for factor-based therapy are hyper-proliferative cells, which cell refer not only to cancer cells, but also to nonmalignant cells which proliferate at rates greater than the rate of cell death. Such therapy may include ex vivo or in vivo embodiments. The details of these embodiments of the present invention, as well as others, are described in more detail in the following sections.

A. Regulation of Cell Growth

Normal cell growth is regulated through a variety of mechanisms. Injury or stress on a cell often has the effect of arresting cells at a particular point in the cell cycle so the cells can recover from the injury or stress. Various cellular factors are known to be activated or produced in response to cell stress including but not limited to factors induced as a result of DNA damage such as DNA repair enzymes (dTMP synthetase, DNA polymerase B, topoismerase I, hMTII-A, DNA ligase IV, DNA ligase III, uracil DNA glycosylase, Ref-1), mediators of apoptosis (p53, bcl-2, WAF1, nitric oxide) and various second messengers.

It has been appreciated for some time that phospholipids play an important role in cellular regulation (Hannun and Bell, 1989). Many breakdown products of membrane lipids including but not limited to diacylglycerol, platelet activating factor, phosphatidic acid, arachidonic acid, prostaglandins, leukotrienes, eicosanoids, thromboxanes, lipoxins, inositol phosphates and inositol glycans are important second messengers and mediators of signal transduction. More recently, the discovery that the breakdown products of sphingophospholipids are biologically active has generated considerable interest in the ability of these molecules to regulate progression through the cell cycle (Hannun and Bell, 1994). These breakdown products, including but not limited to sphingosine and lysosphingolipids, are inhibitors of protein kinase C, a pivotal enzyme in cell regulation and signal transduction.

Activation of sphingomyelinase, a cell membrane sphingolipid, results in the production of ceramide which acts as a second messenger to mediate effects on cell cycle arrest, differentiation and apoptosis. The normal cellular function of ceramide is thought to involve mediation of the effects of normal anti-proliferative factors such as tumor necrosis factor-α. In addition, ceramide appears to mediate anti-proliferative responses and induce cell cycle arrest in response to cellular injury or stress, thereby allowing DNA repair, or sending the cell into the programmed cell death pathway. Mild cellular injury or stress that results in low levels of ceramide may arrest the cell cycle temporarily to allow the cell to recover and repair damage, whereas higher levels of cell injury or stress might induce higher levels of ceramide that would lead to the induction of the apoptotic pathway to destroy the cell. Recently it has been shown that in response to cellular stress, ceramide initiates apoptosis through the stress-activated protein kinase pathway (Verheij et al., 1996). Therefore, events that injure or exert stress on a cell may lead to the induction of cellular factors that mediate either the recovery or the destruction of the affected cell.

B. Anti-Proliferative Factor That Suppresses Cell Growth and its Production

Human cancer cells containing mutant or deleted p53 genes can be transduced with a retroviral vector containing a wild-type p53 protein, resulting in long term stable expression of wild-type p53 protein and subsequent growth arrest (Cai et al., 1993). Since the viral vectors are replication deficient, no transmission of virus occurs following the initial infection. The decrease in cell proliferation observed in such studies was greater than what would have been predicted based on the calculated transduction efficiency of the retroviral vectors employed, however.

When cells transduced with Rv-p53 are mixed with non-transduced cells, containing either mutant or deleted p53, a reduction in cell number and proliferation is observed; this phenomenon is referred to as a "bystander effect." This effect also can be achieved by mixing untransduced cells containing mutant or deleted p53 with the supernatant from Rv-p53 infected cells. Such media supernant is referred to as "cell-conditioned" medium.

In addition to the Rv-p53 vector, cells produce the factor when treated with (i) a replication-defective adenoviral vector expressing wild-type p53, (ii) a plasmid vector expressing wild-type p53 and (iii) an Ad vector expressing β-galactosidase. Based on these observations, it would appear that the factor is not p53 or a molecular breakdown product thereof. Moreover, the fact that the effect is observed with p53-positive, non-malignant fibroblast cells further indicates a non-p53 associated phenomenon. Similarly, it appears that the factor is not retroviral or adenoviral in origin.

Thus, the likely candidate source for the factor is the cell itself. The factor may be produced by the cell in its active form. Alternatively, it may be synthesized as a precursor which is processed as it passes through the cell's excretory machinery or even after it is outside of the cell. It also may be a complex of several molecules that are produced at the same or different times following introduction of the viral or plasmid vector into the cell. These components could then be assembled internally or externally, or both.

Interestingly, stable transfection of cells with a lac-repressible expression cassette encoding wild-type p53 does not appear to induce the bystander effect unless expression of the transgene is induced by the addition of IPTG, which binds the lac repressor and stimulates transcription. This observation suggests that the mere transfer of genetic material into a cell is insufficient to produce the factor but, that possibly, where expression of the transgene also occurs, this particular kind of stress is sufficient to lead to the induction of the bystander activity.

Obviously, where one seeks to produce a large amount of the factor, large scale cell culture techniques will come into play in the production or large quantities of factor-containing cell conditioned medium. Primary mammalian cell cultures techniques are well documented and are disclosed herein by reference (Freshner, 1992). Generally, animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such lower protein production than adherent cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon (Phillips et al., 1985; Mizrahi, 1983). Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

i. Determining "Bystander Activity"

Anti-proliferative activity, cytostatic activity and cytotoxic activity can be measured in various ways. Usually, time course studies will be performed and each data point should be confirmed by duplicate or triplicate samples. First, one may undertake simple cell counts, usually performed as a function of unit volume or based on the total number of cells in a culture container. Counting can be performed by automated analysis, such as FACS, or manually by microscopic methods. Staining of cells is optional, but may improve the ease and accuracy of some methods.

Preferably, inhibition of cell proliferation is as measured by a decrease in $^3$H-thymidine incorporation. A typical study measures the effects observed in cell conditioned medium obtained 24, 48 and 72 hours after the introduction of a transcriptionally active plasmid or viral vector into the cell. The factor appears to be quite stable as its activity is retained in cell conditioned medium after 10 days post-IPTG induction. Thus, studies need not be performed immediately. It also is noted that bystander activity is retained in cell conditioned medium for at least 48 hours after administration of the cell conditioned medium to untreated cells, permitting quantitation of uptake and/or inactivation by certain cells.

ii. Molecular Weight Size Fractionation

Fractionation of the crude cell conditioned medium into soluble and insoluble fractions by centrifugation revealed that the anti-proliferative activity is retained in the soluble fraction of the cell conditioned medium. Size fractionation of the cell conditioned medium using molecular weight cutoff membranes of 300 kD, 100 kD, 50 kD, 30 kD, 10 kD and 3 kD revealed the presence of the factor in all breakthrough fractions as indicated by the reduction in proliferation of tumor cells containing wild type, mutant or deleted p53 gene or protein. Fractionation of the cell conditioned medium by dialysis through membranes of approximately 1000 Da and 500 Da pore size further isolated an anti-proliferative activity to a fraction containing molecules of less than 1000 Da but greater than 500 Da. Further HPLC fractionation over a Pharmacia Biotech Superdex Peptide column with an effective separation range of 100–7000 Da revealed the presence of the anti-proliferative in fractions of high conductivity.

iii. Composition of the Factor

The anti-proliferative factor is a small molecule based on size fractionation and is unlikely to be of viral or p53 origin, based on demonstrable bystander activity observed when cells are contacted with either viral or plasmid vectors with or without p53. In addition, Western blots revealed no evidence of p53 in the soluble fraction of the cell conditioned medium. Thus, further characterization of the composition of the factor is warranted.

Treatment of fractionated cell conditioned medium containing the bystander activity with benzonase, an enzyme that hydrolyzes both single and double stranded nucleic acids, suggests that the activity is not mediated by an RNA or DNA molecule. However, biochemical modification of a nucleic acid by the cell such that it is resistant to nucleases may preclude the complete destruction of all nucleic acids. Further, the anti-proliferative activity may be effected by an oligonucleotide or modified nucleotide that is not affected by benzonase.

Treatment of cell conditioned medium with various proteases including trypsin, proteinase K and pronase, suggests that the activity is not protein in nature. Pronase, which consists essentially of a mixture of proteases, should degrade all polypeptides into individual amino acids. Trypsin and proteinase K cleave amide bonds at specific recognition sites and generate short peptides. However, the anti-proliferative factor may be a peptide or chemically modified proteinaceous molecule that is resistant to the proteases listed above. Based roughly on size fractionation, the size of a peptide would be about 10–12 amino acids, but may be considerably larger or smaller because of the inconsistency of pore size in molecular weight cutoff membranes. It is contemplated by the inventors that if proteinaceous in nature, the anti-proliferative factor may be between one amino acid and 50 amino acids. Biochemical modification such that specific functional groups are added or removed from amino acid residues, including but not limited to phosphates, sulfates and nitrates, may result in a peptide resistant to proteolytic degradation. Similarly, addition or deletion of alkyl, alkenyl, carboxyl, and other such functional groups may be necessary for the functional activation of the anti-proliferative factor.

iv. Stability of the Factor

The biological activity of the anti-proliferative factor is very stable. It is resistant to extreme physical changes including long term storage and multiple freeze/thaw cycles at −80° C., short term storage at 4° C. and boiling at 100° C. for 10 mins. However, it is contemplated by the inventors that more severe treatments such as boiling for extended periods of time may result in the loss of anti-proliferative activity. Lyophilization of cell condition medium containing the anti-proliferative factor does not result in loss of activity after reconstitution in aqueous solution. In addition, it appears to be stable within a pH range from two to 12. Biological activity is not retained in the presence of low or no salt, as evidenced by decrease of anti-proliferative activity after dialyzing against water or $\frac{1}{10}$ isotonic solution. The anti-proliferative factor is concentratable to approximately six-fold and appears to have enhanced activity at higher conductivity levels, suggesting that the factor is stabilized by high ionic interactions. Such ionic interactions may include salt bridges or binding to metal ions; however, high conductivity is not necessary for retention of the anti-proliferative activity since after dialysis into phosphate buffered saline, the factor is still able to suppress the growth of naïve H1299 tumor cells.

V. Isolation, Purification and Detection of the Factor

The methods used in the isolation, purification and identification of the anti-proliferative factor may include any means which are well known in the art. The methods may be, in a general sense, broken down into three different categories. These categories are methods based on physical, immunologic and genetic characteristics of the factor. The latter two are factor specific, i.e., the reagents must be tailored to the factor itself. Physical methods may be factor specific but need not be. A fourth separative approach seeks, in fact, not to physically separate the factor but to destroy any contaminating molecules. This can be performed by using heat, freezing, high pH, or enzymes (lipases, glycosylases, DNAses, RNAses, proteases, etc.). Any of the preceding or following methods may be used in combination to produce various levels of purified factor from a crude cell fraction, a partially purified factor to a factor purified to homogeneity.

a. Physical Separation Methods

Separation of the factor from non-factor components of cells will permit further purification and characterization of the factor. This may be accomplished using methodology that differentiates the physical characteristics of the factor (size, charge, polarity), and includes various chromatographic techniques, gel electrophoresis, chemical partitioning, distillation, crystalization and centrifugation.

Gel electrophoresis involves the migration of the factor through a gel when subjected to an electric field. Generally, the gel is comprised of polyacrylamide or agarose. Migration is usually based on size (e.g., SDS-PAGE) or on ionic character (isoelectric focusing). One may combine two different electrophoretic procedures by performing two dimensional electrophoretic separations in sequence while rotating the axis of migration 90°.

Any of a wide variety of chromatographic procedures may be employed. For example, thin layer chromatography, gas chromatography, high performance liquid chromatography, paper chromatography, affinity or pseudo-affinity chromatography, supercritical flow chromatography, gel chromatography or ion exchange chromatograph may be employed.

Partition chromatography is based on the theory that if two phases are in contact with one another, and if one or both phases constitute a solute, the solute will distribute itself between the two phases. Usually, partition chromatography employs a column which is filled with a sorbent and a solvent. The solution containing the solute is layered on top of the column. The solvent is then passed through the column, continuously, which permits movement of the solute through the column material. The solute can then be collected based on its movement rate. The two most common types of partition chromatograph are paper chromatograph and thin-layer chromatograph (TLC); together these are called adsorption chromatography. In both cases, the matrix contains a bound liquid. Other examples of partition chromatography are gas-liquid and gel chromatography.

Paper chromatography is a variant of partition chromatography that is performed on cellulose columns in the form of a paper sheet. Cellulose contains a large amount of bound water even when extensively dried. Partitioning occurs between the bound water and the developing solvent. Frequently, the solvent used is water. Usually, very small volumes of the solution mixture to be separated is placed at top of the paper and allowed to dry. Capillary draws the solvent through the paper, dissolves the sample, and moves the components in the direction of flow. Paper chromatograms may be developed for either ascending or descending solvent flow. Two dimensional separations are permitted by changing the axis of migration 90° after the first run.

Thin layer chromatography (TLC) is very commonly used to separate lipids and, therefore, is considered a preferred embodiment of the present invention. TLC has the advantages of paper chromatography, but allows the use of any substance that can be finely divided and formed into a uniform layer. In TLC, the stationary phase is a layer of sorbent spread uniformly over the surface of a glass or plastic plate. The plates are usually made by forming a slurry of sorbent that is poured onto the surface of the gel after creating a well by placing tape at a selected height along the perimeter of the plate. After the sorbent dries, the tape is removed and the plate is treated just as paper in paper chromatography. The sample is applied and the plate is contacted with a solvent. Once the solvent has almost reached the end of the plate, the plate is removed and dried. Spots can then be identified by fluorescence, immunologic identification, counting of radioactivity, or by spraying varying reagents onto the surface to produce a color change.

In Gas-Liquid chromatography (GLC), the mobile phase is a gas and the stationary phase is a liquid adsorbed either to the inner surface of a tube or column or to a solid support. The liquid usually is applied as a solid dissolved in a volatile solvent such as ether. The sample, which may be any sample that can be volatized, is introduced as a liquid with an inert gas, such as helium, argon or nitrogen, and then heated. This gaseous mixture passes through the tubing. The vaporized compounds continually redistribute themselves between the gaseous mobile phase and the liquid stationary phase, according to their partition coefficients.

The advantage of GLC is in the separation of small molecules. Sensitivity and speed are quite good, with speeds that approach 1000 times that of standard liquid chromatography. By using a non-destructive detector, GLC can be used preparatively to purify grams quantities of material. The principal use of GLC has been in the separation of alcohols, esters, fatty acids and amines.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

The gel material for gel chromatography is a three-dimensional network whose structure is usually random. The gels consist of cross-linked polymers that are generally inert, do not bind or react with the material being analyzed, and are uncharged. The space filled within the gel is filled with liquid and this liquid occupies most of the gel volume. Common gels are dextran, agarose and polyacrylamide; they are used for aqueous solution.

High Performance Liquid Chromatography (HPLC) is characterized by a very rapid separation with extraordinary resolution of peaks. This is achieved by the use of very fine particles and high pressure to maintain and adequate flow rate. Separation can be accomplished in a matter of minutes, or a most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

Chemical partitioning refers to the tendency of a compound to partition with certain chemicals of a like nature. A classic example of this approach is the use of organic and inorganic solvents to facilitate the partition of a chemical species. Using a wide variety of different solvents, having differing chemical properties, it is possible to differentially separate a chemical compound. Another form of partitioning uses chemical to result in a phase separation of a compound of interest. A classic example of this embodiment is the use of ammonium sulfate to cause the precipitation of certain proteins (e.g., antibodies) out of a complex protein mixture. Other versions of this approach are well known to those of skill in the art.

Yet another method for separating the factor involves centrifugation. Centrifugation involves the separation of the species based on its buoyancy/specific density or hydrodynamic radius. Various different solvents are used, depending on the desired effect. For example, CsCl and Percoll™ form common solutions for achieving density-dependent centrifugal separation. Sucrose (step or continuous) gradients are used to exploit differences in the buoyancy. Other centrifugation solutions are known to those of skill in the art.

b. Antibodies and Immunologic Methods

Antibodies against the factor of the present invention produced and isolated using the methodology described below will be useful in the present invention, primarily in assays for the detection of the factor and in isolating the factor. In addition, certain antibodies may themselves prove to have activity on their own. Means for preparing and characterizing antibodies are well known in the art (see, e.g., Antibodies: A Laboratory Manual, Cold Spring Harbor Laboratory, 1988; incorporated herein by reference).

The methods for generating monoclonal antibodies (MAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat.

Immunogenic compositions of the factor include crudely fractionated preparations, partially purified factor and the factor purified to homogeneity. As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a compound to a carrier protein are well known in the art and include glutaraldehyde, m-maleimidobenzoyl-N-hydroxysuccinimide ester, carbodiimyde and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or the animal can be used to generate MAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages, but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Mycloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Campbell, pp. 75–83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1976), and those using polyethylene glycol (PEG), such as 37% (v/v) PEG, by Gefter et al. (1977). The use of electrically induced fusion methods is also appropriate.

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid. Radioimmunoassays, enzyme immunoassays, cytotoxicity assays, plaque assays, dot immunobinding assays, and the like, may be used.

Where one desires to generate an antibody with defined activity, one would generally screen the candidate hybridomas to identify those hybridomas that produce antibodies that have the desired inhibitory or stimulatory properties. Any selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

Immunoassays encompassed by the present invention include, but are not limited to those described in U.S. Pat. No. 4,367,110 (double monoclonal antibody sandwich assay) and U.S. Pat. No. 4,452,901 (Western blot). Other assays include immunoprecipitation of labeled ligands and immunocytochemistry, both in vitro and in vivo.

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful.

It is contemplated that antibodies may be generated against the anti-proliferative factor by any methods that are well known in the art, including but not limited to injecting an isolated fraction into rabbits or mice to generate polyclonal serum. It is further contemplated that in an ELISA, antibodies reactive with the anti-proliferative factor are immobilized onto a selected surface exhibiting protein affinity, such as a well in a polystyrene microtiter plate. Then, a test composition containing the desired antigen, such as a cell conditioned medium, is added to the wells. After binding and washing to remove non-specifically bound immune complexes, the bound antigen may be detected. Detection is generally achieved by the addition of another antibody, specific for the desired antigen, that is linked to a detectable label. This type of ELISA is a simple "sandwich ELISA". Detection may also be achieved by the addition of a second antibody specific for the desired antigen, followed by the addition of a third antibody that has binding affinity for the second antibody, with the third antibody being linked to a detectable label.

Variations of ELISA techniques are known to those of skill in the art. In one such variation, the samples containing the desired antigen are immobilized onto the well surface and then contacted with the antibodies of the invention. After binding and appropriate washing, the bound immune complexes are detected. Where the initial antigen specific antibodies are linked to a detectable label, the immune complexes may be detected directly. Again, the immune complexes may be detected using a second antibody that has binding affinity for the first antigen specific antibody, with the second antibody being linked to a detectable label.

Competition ELISAs are also possible in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal.

Irrespective of the format employed, ELISAs have certain features in common, such as coating, incubating or binding, washing to remove non-specifically bound species, and detecting the bound immune complexes. These are described below.

Antigen or antibodies may also be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of the antigen or antibody to the well, coating with a non-reactive material to reduce background, and washing to remove unbound material, the immobilizing surface is contacted with the clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The suitable conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C.

Following all incubation steps in an ELISA, the contacted surface is washed so as to remove non-complexed material. Washing often includes washing with a solution of PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation, e.g., incubation for 2 hours at room temperature in a PBS-containing solution such as PBS/Tween.

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

Alternatively, the label may be a chemiluminescent one. The use of such labels is described in U.S. Pat. Nos. 5,310,687, 5,238,808 and 5,221,605.

Assays for the production of anti-proliferative factor by a cell also can be determined in normal/abnormal tissue for diagnostic purposes and as a measure of the efficacy of the induction of the factor. Methods for in vitro and in situ analysis are well known and involve assessing binding of antigen-specific antibodies to tissues, cells or cell extracts. These are conventional techniques well within the grasp of those skilled in the art. For example, antibodies to anti-proliferative factor may be used in conjunction with both fresh-frozen and formalin-fixed, paraffin-embedded tissue blocks prepared for study by immunohistochemistry (IHC).

Each tissue block may consist of 50 mg of residual "pulverized" tumor. The method of preparing tissue blocks from these particulate specimens has been successfully used in previous IHC studies of various prognostic factors, e.g., in breast cancer, and is well known to those of skill in the art. (Abbondanzo et al., 1990; Allred et al., 1990; Brown et al., 1990).

Briefly, frozen-sections may be prepared by rehydrating 50 ng of frozen pulverized tumor at room temperature in PBS in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25–50 serial sections containing an average of about 500 remarkably intact tumor cells.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

c. Southern and Northern Blotting Techniques: PCR

Southern and Northern blotting are commonly used techniques in molecular biology and well known within the grasp of one skilled in the art.

For Southern blots, the DNA from test cells is recovered by gentle cell rupture in the presence of a cation chelator such as EDTA. The proteins and other cell milieu are removed by admixing with saturated phenol or phenol/chloroform and centrifugation of the emulsion. The DNA is in the upper aqueous phase; it is deproteinised and mixed with ethanol. This solution allows the DNA to precipitate, and the DNA can then be recovered using centrifugation.

Electrophoresis in agarose or polyacrylamide gels is the most usual way to separate DNA molecules. Southern blotting will confirm the identity of the anti-proliferative factor encoding DNA. This is achieved by transferring the DNA from the intact gel onto nitrocellulose paper. The nitrocellulose paper is then washed in buffer that has for example, a radiolabelled cDNA containing a sequence complementary to the anti-proliferative factor DNA. Such probes may be identified through direct sequencing of proteins or fragments thereof and genomic library screening. The probe binds specifically to the DNA that encodes at least a portion of anti-proliferative factor and can be detected using autoradiography by contacting the probed nitrocellulose paper with photographic film.

Anti-proliferative factor encoding mRNA can be detected in a similar manner by a process known as Northern blotting. For more detailed description of buffers, gel preparation, electrophoresis conditions, etc., the skilled artisan is referred to Sambrook et al. (1989).

PCR is a powerful tool in modern analytical biology. Short oligonucleotide sequences usually 15–35 bp in length are designed, homologous to flanking regions either side of the sequences to be amplified. Primers are added in excess to the source DNA, in the presence of buffer, enzyme, and free nucleotides. The source DNA is denatured at 9520 C. and then cooled to 40–5020 C. to allow the primers to anneal. The temperature is adjusted to the optimal temperature for the polymerase for an extension phase. This cycle is repeated 25–40 times. The technique of PCR is well known and the methods disclosed herein can be readily adapted for each unique situation by one skilled in the art.

Any other methods that are known to those skilled in the art may be employed for the isolation, purification, and identification of the anti-proliferative factor including but not limited to techniques involving organic and soluble phase separation, column chromatography using lectins, antibodies, ion exchange resins, other separation matrices, or tags reactive with specific chemical species, HPLC analysis and spectrophotometry. It is also contemplated by the inventors that once the anti-proliferative factor is identified it may be routinely isolated from cells that have been induce to biologically synthesize it or chemically synthesized by any of several well known means including oligonucleotide, peptide, or organic chemistry synthesis.

C. Treatment of Cancers Using the Anti-Proliferative Factor

A subject presenting a with a malignancy may be treated with the anti-proliferative factor of the present invention. Patients may, but need not, have received previous chemo-, radio- or genetic therapies. Optimally, patients will have adequate bone marrow function (defined as peripheral absolute granulocyte count of >2,000/mm$^3$ and platelet count of 100,000/mm$^3$), adequate liver function (bilirubin $\leq 1.5$ mg/dl) and adequate renal function (creatine <1.5 mg/dl). The determination of suitability for treatment will, ultimately, be up to the attending clinician.

The patient will be treated with a pharmaceutically acceptable form of anti-proliferative factor or a functional analog thereof. This administration could be in the form of, for example, an intratumoral injection, or indeed any other method of application that is routinely used and well known to one of skill in the art, e.g., systemic or intravenously. Obviously, the best manner by which a given tumor is treated will depend on its location and character (e.g., invasive, vascularized, necrotic). A biopsy of the lesions to be injected may be performed and the tissue stored for immunohistochemistry analyses.

The unit dose of anti-proliferative factor typically will be reconstituted into a pharmaceutically acceptable form immediately prior to, or, because of the observed stability of the anti-proliferative factor, days to weeks prior to administration. The starting dose may vary depending on the specific activity of the particular preparation of the anti-proliferative factor, size of the tumor, the rate at which the tumor is growing, etc. It is envisioned that the treatment will be administered over a period of time typical of conventional cancer therapies ranging from single to multiple doses. During this time, the patient will be monitored for absence of tumor progression, response or toxicity and the doses adjusted accordingly.

i. Pharmaceutical Compositions and Routes of Administration

Aqueous compositions of the present invention will have an effective amount of the factor or factors. An effective amount is defined as that amount of the factor that will achieve a detectable effect such as cytotoxicity, cytostaticity or blocking of cell proliferation. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and anti-fungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including cremes, lotions, mouthwashes, inhalants and the like.

The active compounds of the present invention will often be formulated for parenteral administration, e.g., formulated for injection via the intravenous, intramuscular, subcutaneous, or even intraperitoneal routes. The preparation of an aqueous composition that contains a compound or compounds that decreases the proliferation rate of cells will be within the skill of those in the art, in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and anti-fungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum mono-stearate and gelatin.

Sterile injectable solutions are prepared by incorporating the active compounds in the required amount in the appropriate solvent with various of the other ingredients enumerated above, as required, followed by filter sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in cremes and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary, and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

ii. Kits

All the essential materials and reagents required for administering the anti-proliferative factor may be assembled together in a kit. When the components of the kit are provided in one or more liquid solutions, the liquid solution preferably is an aqueous solution, with a sterile aqueous solution being particularly preferred.

For in vivo use, as discussed below, the factor may be provided in combination with a gene therapy vector or chemo- or radiotherapeutic agent. These normally will be a separate formulation, but may be formulated into a single pharmaceutically acceptable composition. The container means may itself be geared for administration, such as an inhalant, syringe, pipette, eye dropper, or other such like apparatus, from which the formulation may be applied to an infected area of the body, such as the lungs, or injected into an animal, or even applied to and mixed with the other components of the kit.

The compositions of these kits also may be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining administration of the agent and explaining how the agent will decrease proliferation of cells, and explaining how the expression of the gene therapy agents causes the anti-proliferative factor to be produced.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with a separate instrument for assisting with the injection/administration or placement of the ultimate complex composition within the body of an animal. Such an instrument may be an inhalant, syringe, pipette, forceps, measured spoon, eye dropper or any such medically approved delivery vehicle. Other instrumentation includes devices that permit the reading or monitoring of reactions in vitro.

D. Treatment of Cells using Anti-Proliferative Factor in Combination with Gene Therapy In a separate embodiment of the present invention, it is envisioned that anti-proliferative factor will be used in combination with conventional gene therapy in the treatment of cancer and other cell proliferative disorders.

It is clear that delivery of a plasmid or viral vector encoding a gene into a cell can result in production of an anti-proliferative factor. As stated above, in one embodiment of the invention, the anti-proliferative factor is produced, isolated and administered to the cells. In yet another version, however, the factor is used along with a plasmid or viral vector encoding a gene. This can be accomplished two ways. First, the factor may be isolated as described, and then contacted with a cell that has, is or will be treated according to a gene therapy protocol. Thus, the production of the factor as a result of the transgene therapy is not necessary. Alternatively, the factor may be induced by the administration of the gene therapy vector.

It is envisioned that the gene therapy vector may encode p53, in the case of gene therapy of p53 mutated cancers, or some other appropriate gene specific to a particular cancer or proliferative disorder. Other genes currently in use or contemplated for use in the treatment of cancer include but are not limited to C-CAM, RB, $p16^{INK4}$, $p21^{WAF1}$, WT-1, BRCA-1, BRCA-2, bcr-abl, HSV-tk, HLA-B7, antisense K-ras, antisense-myc, antisense-fos, anti-IGF-1, IL-2 and cytosine deaminase. As stated above, the anti-proliferative factor can be administered concurrently with the gene therapy, before the gene therapy or after the gene therapy. All the components of the gene therapy and the therapeutic anti-proliferative factor compositions can be put together in kit form as described above. Elements utilized for inducation of the factor and/or gene therapy are described below.

i. Expression Vectors

Throughout this application, the term "expression construct" is meant to include any type of genetic construct containing a nucleic acid coding for a gene product in which part or all of the coding sequence is capable of being transcribed and subsequently translated into a protein.

In order for the construct to effect expression of a gene transcript, the polynucleotide encoding the gene will be under the transcriptional control of a promoter. A "promoter" refers to a DNA sequence recognized by the synthetic machinery of the host cell, or introduced synthetic machinery, that is required to initiate the specific transcription of a gene. The phrase "under transcriptional control" means that the promoter is in the correct location in relation to the polynucleotide to control RNA polymerase initiation and expression of the polynucleotide.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter that is employed to control the expression of a polynucleotide is not believed to be critical, so long as it is capable of expressing the polynucleotide in the targeted cell. Thus, where a human cell is targeted, it is preferable to position the polynucleotide coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used to obtain high-level expression of the p53 gene or polynucleotide. The use of other viral or mammalian cellular or bacterial phage promoters which are well known in the art to achieve expression of polynucleotides is contemplated as well, provided that the levels of expression are sufficient to produce a growth inhibitory effect.

By employing a promoter with well known properties, the level and pattern of expression of a polynucleotide following transfection can be optimized. For example, selection of a promoter which is active in specific cells, such as tyrosinase (melanoma), alpha-fetoprotein and albumin (liver tumors), CC10 (lung tumor) and prostate-specific antigen (prostate tumor) will permit tissue-specific expression of the polynucleotides. Table 1 lists several elements/promoters which may be employed, in the context of the present invention, to regulate the expression of genetic constructs. This list is not intended to be exhaustive of all the possible elements involved in the promotion of gene expression but, merely, to be exemplary thereof.

Enhancers were originally detected as genetic elements that increased transcription from a promoter located at a distant position on the same molecule of DNA. This ability to act over a large distance had little precedent in classical studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a p53 construct. Use of a T3, T7 or SP6 cytoplasmic expression system is another possible embodiment. Eukaryotic cells can support cytoplasmic transcription from certain bacteriophage promoters if the appropriate bacteriophage polymerase is provided, either as part of the delivery complex or as an additional genetic expression vector.

TABLE 1

PROMOTERS

Immunoglobulin Heavy Chain
Immunoglobulin Light Chain
T-Cell Receptor
HLA DQ α and DQ β
β-Interferon
Interleukin-2
Interleukin-2 Receptor
MHC Class II 5
MHC Class II HLA-DRα
β-Actin
Muscle Creatine Kinase
Pre-albumin (Transthyretin)
Elastase I
Metallothionein
Collagenase
Albumin Gene
α-Fetoprotein
τ-Globin
β-Globin
c-fos
c-HA-ras
Insulin
Neural Cell Adhesion Molecule (NCAM)
$α_1$-Antitrypsin
H2B (TH2B) Histone
Mouse or Type I Collagen
Glucose-Regulated Proteins (GRP94 and GRP78)
Rat Growth Hormone
Human Serum Amyloid A (SAA)
Troponin I (TN I)
Platelet-Derived Growth Factor
Duchenne Muscular Dystrophy
SV40
Polyoma
Retroviruses
Papilloma Virus
Hepatitis B Virus
Human Immunodeficiency Virus
Cytomegalovirus Further, selection of a promoter that is regulated in response to specific physiologic signals can permit inducible expression of the p53 construct. For example, with the polynucleotide under the control of the human PAI-1 promoter, expression is inducible by tumor necrosis factor. Table 2 illustrates several promoter/inducer combinations:

TABLE 2

| Element | Inducer |
| --- | --- |
| MT II | Phorbol Ester (TPA) Heavy metals |
| MMTV | Glucocorticoids |
| β-Interferon | poly(rI)X, poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |

In certain embodiments of the invention, the delivery of an expression vector in a cell may be identified in vitro or in vivo by including a marker in the expression vector. The marker would result in an identifiable change to the transfected cell permitting easy identification of expression. Usually the inclusion of a drug selection marker aids in cloning and in the selection of transformants. Alternatively, enzymes such as herpes simplex virus thymidine kinase (tk) (eukaryotic) or chloramphenicol acetyltransferase (CAT) (prokaryotic) may be employed. Immunologic markers also can be employed. The selectable marker employed is not believed to be important, so long as it is capable of being expressed along with the polynucleotide encoding the gene of interest. Further examples of selectable markers are well known to one of skill in the art.

One will typically include a polyadenylation signal to effect proper polyadenylation of the transcript. The nature of the polyadenylation signal is not believed to be crucial to the successful practice of the invention, and any such sequence may be employed. Also contemplated as an element of the expression construct is a terminator. These elements can serve to enhance message levels and to minimize read through from the construct into other sequences.

In preferred embodiments of the present invention, the expression construct comprises a virus or engineered construct derived from a viral genome. The ability of certain viruses to enter cells via receptor-mediated endocytosis and, in some cases, integrate into the host cell chromosomes, have made them attractive candidates for gene transfer into mammalian cells. However, because direct uptake of naked DNA has been demonstrated, as well as receptor-mediated uptake of DNA complexes (discussed below), expression vectors need not be viral but, instead, may be any plasmid, cosmid or phage construct that is capable of supporting expression of encoded genes in mammalian cells, such as pUC or Bluescript™ plasmid series.

a. Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol, and env—that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding the gene of interest is inserted into the viral genome in the place of certain viral sequences to produce a virus that is replication-defective. In order to produce virions, a packaging cell line containing the gag, pol and env genes but without the LTR and Ψ components is constructed (Mann et al., 1983). When a recombinant plasmid containing a human cDNA, together with the retroviral LTR and Ψ sequences is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of galactose residues to the viral envelope. This modification could permit the specific infection of hepatocytes via asialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

b. Adenoviruses

Human adenoviruses are double-stranded DNA tumor viruses with genome sizes of approximate 36 kb (Tooze, 1981). As a model system for eukaryotic gene expression, adenoviruses have been widely studied and well characterized, which makes them an attractive system for development of adenovirus as a gene transfer system. This group of viruses is easy to grow and manipulate, and exhibit a broad host range in vitro and in vivo. In lytically infected cells, adenoviruses are capable of shutting off host protein synthesis, directing cellular machineries to synthesize large quantities of viral proteins, and producing copious amounts of virus.

The E1 region of the genome includes E1A and E1B which encode proteins responsible for transcription regulation of the viral genome, as well as a few cellular genes. E2 expression, including E2A and E2B, allows synthesis of viral replicative functions, e.g. DNA-binding protein, DNA polymerase, and a terminal protein that primes replication. E3 gene products prevent cytolysis by cytotoxic T cells and tumor necrosis factor and appear to be important for viral propagation. Functions associated with the E4 proteins include DNA replication, late gene expression, and host cell shutoff. The late gene products include most of the virion capsid proteins, and these are expressed only after most of the processing of a single primary transcript from the major late promoter has occurred. The major late promoter (MLP) exhibits high efficiency during the late phase of the infection (Stratford-Perricaudet and Perricaudet, 1991).

As only a small portion of the viral genome appears to be required in cis (Tooze, 1981), adenovirus-derived vectors offer excellent potential for the substitution of large DNA fragments when used in connection with cell lines such as 293 cells. Ad5-transformed human embryonic kidney cell lines (Graham, et al., 1977) have been developed to provide the essential viral proteins in trans. The inventor thus reasoned that the characteristics of adenoviruses rendered them good candidates for use in targeting cancer cells in vivo (Grunhaus & Horwitz, 1992).

Particular advantages of an adenovirus system for delivering foreign genes or proteins to a cell include (i) the ability to substitute relatively large pieces of viral DNA by foreign DNA; (ii) the structural stability of recombinant adenoviruses; (iii) the safety of adenoviral administration to humans; and (iv) lack of any known association of adenoviral infection with cancer or malignancies; (v) the ability to obtain high titers of the recombinant virus; and (vi) the high infectivity of adenovirus.

Further advantages of adenovirus vectors over retroviruses include the higher levels of gene expression. Additionally, adenovirus replication is independent of host gene replication, unlike retroviral sequences. Because adenovirus transforming genes in the E1 region can be readily deleted and still provide efficient expression vectors, oncogenic risk from adenovirus vectors is thought to be negligible (Grunhaus & Horwitz, 1992).

In general, adenovirus gene transfer systems are based upon recombinant, engineered adenovirus which is rendered replication-incompetent by deletion of a portion of its genome, such as E1, and yet still retains its competency for infection. Sequences encoding relatively large foreign proteins can be expressed when additional deletions are made in the adenovirus genome. For example, adenoviruses deleted in both E1 and E3 regions are capable of carrying up to 10 Kb of foreign DNA and can be grown to high titers in 293 cells (Stratford-Perricaudet and Perricaudet, 1991). Surprisingly persistent expression of transgenes following adenoviral infection has also been reported.

c. Other Vectors as Expression Constructs

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpes viruses may be employed. These viruses offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. in vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et. al., 1991).

i. Alternative Methods for Gene Delivery

In order to effect expression of gene constructs, the expression vector must be delivered into a cell. As described above, one mechanism for delivery is via viral infection where the expression vector is encapsidated in an infectious adenovirus particle.

Several non-viral methods for the transfer of expression vectors into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), polycations (Boussif et al., 1995) and receptor-mediated transfection (Wu and Wu, 1987; Wu and Wu, 1988). Some of these techniques may be successfully adapted for in vivo or ex vivo use.

In one embodiment of the invention, the adenoviral expression vector may simply consist of naked recombinant vector. Transfer of the construct may be performed by any of the methods mentioned above which physically or chemically permeabilize the cell membrane. For example, Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding other genetic constructs may also be transferred in a similar manner in vivo.

Another embodiment of the invention for transferring a naked DNA expression vector into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ. A DNA construct encoding the desired gene may be delivered via this method.

In a further embodiment of the invention, the expression vector may be entrapped in a liposome. Liposomes are vesicular structures characterized by a phospholipid bilayer membrane and an inner aqueous medium. Multilamellar liposomes have multiple lipid layers separated by aqueous medium. Liposomes form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated polynucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression vectors have been successfully employed in transfer and expression of a polynucleotide in vitro and in vivo, then they are applicable for the present invention. Where a bacteriophage promoter is employed in the DNA construct, it also will be desirable to include within the liposome an appropriate bacteriophage polymerase.

Another mechanism for transferring expression vectors into cells is receptor-mediated delivery. This approach takes advantage of the selective uptake of macromolecules by receptor-mediated endocytosis in almost all eukaryotic cells. Because of the cell type-specific distribution of various receptors, the delivery can be highly specific (Wu and Wu, 1993). Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1993). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that an adenoviral expression vector also may be specifically delivered into a cell type such as lung, epithelial or tumor cells, by any number of receptor-ligand systems, with or without liposomes. For example, epidermal growth factor (EGF) may be used as the receptor for mediated delivery of the desired gene construct in many tumor cells that exhibit up-regulation of EGF receptor. Galactose can be used to target the asialoglycoprotein receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a polynucleotide into the cells, in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods. During ex vivo culture, the expression vector can express the designated gene construct. Finally, the cells may be reintroduced into the original animal, or administered into a distinct animal, in a pharmaceutically acceptable form by any of the means described below.

E. Combination With Standard Chemo- and Radiotherapy

Tumor cell resistance to DNA damaging agents represents a major problem in clinical oncology. One goal of current cancer research is to find ways to improve the efficacy of chemo- and radiotherapy by combining it with gene therapy. In the context of the present invention, it is contemplated that anti-proliferative factor enhanced gene therapy could be used similarly in conjunction with chemo- or radiotherapeutic intervention. In addition is it contemplated that anti-proliferative factor could be used with or without gene therapy, and in combination with chemo- or radiotherapy. For example in those instances where gene therapy is not a viable treatment for a particular type of cancer.

To kill or halt proliferation of cells, such as malignant or metastatic cells, using the methods and compositions of the present invention, one will contact a "target" cell with the anti-proliferative factor and a gene therapy vector and, optionally, with at least one chemotherapeutic agent, e.g., a DNA-damaging agent. These compositions would be provided in a combined amount effective to kill or inhibit proliferation of the cell. This process may involve contacting the cells with the anti-proliferative factor and the chemotherapeutic or radiotherapeutic agent(s) at the same time. This may be achieved by contacting the cell with a single composition or pharmacological formulation that includes both factor and chemotherapeutic or by irradiating the patient while the factor is administered. Alternatively, with a chemotherapeutic combination, this may be accomplished by the cell with two distinct compositions or formulations, at the same time, wherein one composition includes the anti-proliferative factor and the other includes the chemotherapeutic agent.

Alternatively, the anti-proliferative factor treatment may precede or follow the radio- or chemotherapeutic treatment by intervals ranging from minutes to weeks. In embodiments where the DNA-damaging agent and anti-proliferative factor are applied separately to the cell, one would generally ensure that a significant period of time did not expire between the time of each delivery, such that the DNA damaging agent and anti-proliferative factor would still be able to exert an advantageously combined effect on the cell. In such instances, it is contemplated that one would contact the cell with both agents within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either anti-proliferative factor or the chemotherapeutic agent will be desired. Various combinations may be employed where anti-proliferative factor and the chemotherapeutic agent is "B":

| | | | | | |
|---|---|---|---|---|---|
| A/B/A | B/A/B | B/B/A | A/A/B | A/B/B | B/A/A |
| B/B/B/A | B/B/A/B | A/A/B/B | A/B/A/B | A/B/B/A | B/B/A/A |
| B/A/B/A | B/A/A/B | A/A/A/B | B/A/A/A | A/B/A/A | A/A/B/A |
| A/B/B/B | B/A/B/B | | | | |

One may also read the "A" or "B" features above to include gene therapy, thereby creating a tripartite therapy. Also, the "A" and "B" designations may used, in conjunction with the preceding section on gene therapy combination with the anti-proliferative factor, to define sequential treatments with those two agents.

The terms "contacted" and "exposed," when applied to a cell, are used herein to describe the process by which a material, such as anti-proliferative factor and a chemotherapeutic agent or factor are delivered to a target cell or are placed in direct juxtaposition with the target cell. To achieve cell killing or inhibition of proliferation, both agents are delivered to a cell in a combined amount effective to kill the cell or inhibit its proliferation.

In particular, the present invention will employ DNA damaging agents as part of a combined therapy protocol. DNA damaging agents or factors are defined herein as any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents", function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide. In certain embodiments, the use of cisplatin in combination with anti-proliferative factor and a p53 protein or gene is particularly preferred as this compound.

Any method also may be used to contact a cell with anti-proliferative factor and a gene therapy vector, so long as the method results in enhanced reduction in proliferation of the cell. This includes both the direct delivery of a specific protein to the cell and the delivery of a gene or DNA segment that encodes a specific protein, which gene will direct the expression and production of the protein within the cell. In that protein delivery is subject to such drawbacks as protein degradation and low cellular uptake, it is contemplated that the use of a recombinant vector that expresses the particular protein will provide particular advantages.

In treating cancer according to the invention, one would contact the tumor cells with a chemotherapeutic agent in addition to the anti-proliferative factor and gene therapy vector. This may be achieved by irradiating the localized tumor site with DNA damaging radiation such as X-rays, UV-light, γ-rays or even microwaves. Alternatively, the tumor cells may be contacted with the DNA damaging agent by administering to the subject a therapeutically effective amount of a pharmaceutical composition comprising a DNA damaging compound such as, adriamycin, 5-fluorouracil, etoposide, camptothecin, actinomycin-D, mitomycin C, or more preferably, cisplatin. The DNA damaging agent may be prepared and used as a combined therapeutic composition, or kit, by combining it with anti-proliferative factor and/or gene therapy vector, as described above.

Agents that directly cross-link nucleic acids, specifically DNA, are envisaged and are shown herein, to eventuate DNA damage leading to a synergistic anti-neoplastic combination. Agents such as cisplatin, and other DNA alkylating may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis, and chromosomal segregation. Such chemotherapeutic compounds include adriamycin, also known as doxorubicin, etoposide, verapamil, podophyllotoxin, and the like. Widely used in clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of nucleic acid precursors, and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the regional delivery of anti-proliferative factor and anti-cancer gene therapy vectors to cancer cells in patients will be a very efficient method for increasing the therapeutical efficacy of gene therapy. Similarly, the chemo- or radiotherapy may be directed to a particular, affected region of the subject's body. Alternatively, systemic delivery of anti-proliferative factor and a gene therapy vector, or the DNA damaging agent may be appropriate in certain circumstances, for example, where extensive metastasis has occurred.

F. Treatment of Hyper-Proliferative Disorders

In yet another embodiment of the invention, it is proposed that the anti-proliferative factor will be used in the treatment of hyper-proliferative disorders beyond that of cancer. Such disorders include but are not limited to glaucoma, psoriasis, rheumatoid arthritis, restenosis, inflammatory bowel disease, and chemotherapy-induced alopecia and mucositis.

For example, the present invention provides a method for the treatment of restenosis through administration of the anti-proliferative factor, alone and in combination with specific gene therapy protocols. For the purposes of this invention any blood vessel injured sufficiently to cause neointima formation is contemplated as an injured blood vessel. These injuries may be the result of, but are not limited to, angioplasty, arterial reconstruction, stent implantation, and atherectomy.

The administration of the anti-proliferative factor alone or in combination with gene therapy can be performed prior to the time of injury, concurrently with the time of injury, or after the time of injury. It is preferred that the administration period be within approximately one week prior to injury to approximately four weeks after injury. A more preferable time period of administration is approximately from the time of injury to 15 to 20 days after the time of injury. Ideally, the therapy will be administered at the time when the smooth muscle cells are actively proliferating. In practice, it is likely that the administration of the therapy will be performed at the time of injury directly at the site of the injury.

Administration to the site of injury refers to placing in direct contact the anti-proliferative factor with or without gene therapy construct with the damaged wall of the blood vessel, thereby increasing the likelihood of the anti-proliferative factor or gene therapy construct coming in contact with proliferating smooth muscle cells. It is preferred that the therapy be administered in such a manner that the anti-proliferative factor and gene therapy construct remain at the site of injury for sufficient time to result in the inhibition of smooth muscle cell growth, thus preventing re-obstruction of the lumen of the vessel. The time period of such contact is preferred to be between one minute to several hours, and more preferably to be between one minute and 60 minutes.

The route of administration can be any method that provides for the contact of the anti-proliferative factor and gene therapy vector with the site of injury, including but not limited to intravenously, subcutaneously, intramuscularly, or intraarterially. It is preferred that the therapy be administered intraarterially through catheters located directly at the site of injury, thus providing direct contact with the injured vessel. However, any other such method that places in close proximity the anti-proliferative factor and gene therapy vector with the injured vessel wall, is contemplated by the inventors.

It is envisioned that the application of gene therapy to the treatment of restenosis will involve the administration of a gene therapy vector encoding a gene that inhibits the proliferation of cells. Such genes include but are not limited to herpes simplex virus thymidine kinase (HSV-TK), cytosine deaminase, dominant-negative ras and nitric oxide synthase. Other such genes that encode proteins that play a role in cell cycle progression are contemplated by the inventors. In addition, it is contemplated that a gene therapy construct encoding an antisense molecule that may interfere with the expression of normal cellular factors involved in cell cycle progression will be useful in the present invention. Such genes include but are not limited to oligo- and polynucleotides derived from c-myc, CDC2 and MAP kinase. Combinations of such gene therapy with prodrugs, for example HSV-TK and gancyclovir, which upon expression of the HSV-TK gene will render the prodrug gancyclovir cytotoxic, are also contemplated by the inventors as providing utility for the inhibition of cell growth.

Similar strategies using anti-proliferative factor alone or in combination with gene therapy for the treatment of other hyper-proliferative disorders, as previously disclosed, are envisioned for the present invention. It is contemplated that the method of treatment will involve the gene therapy vectors, routes of administration, time of administration and other methods previously disclosed in the present specification.

G. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Materials and Methods

This example relates the examples of the methods used in the practice of the present invention.

a. Cell Lines and Tissue Culture

Non-small cell lung cancer cell lines H460 (wild type p53), H358 (p53 null), H322 (p53 mutant), were obtained from Dr. Adi Gazdar and John Minm. H226Br (p53 null) cell lines were obtained from Dr. Isiah Fidler. H1299 (p53 null) and Saos-2 (p53 null) cells were obtained from ATCC (Rockville, Md.). MJ cells are human foreskin fibroblasts and were obtained from Dr. Olivia Pereira Smith. ITIC1 cells are H1299 cells that have been stably co-transfected with the pIN92 and p3'SS plasmids (see below). All cell lines were grown in DMEM medium containing 5–10% FBS and incubated at 5% $CO_2$. All studies were done when cells were at a confluency of 5% to 20%. Specific details are noted appropriately.

b. Virus and Plasmids

Two adenoviral constructs, Adp53 and Adβgal were used in the present invention. Both constructs consisted of the Ad5 genome containing a partially deleted E1 region to render them replication incompetent. Inserted into the Ad5 genome were either wild type p53 cDNA or a β-galactosidase gene, under the control of a CMV promoter and an SV40 poly-A signal. The recombinant adenovirus was propagated in 293 cells and purified essentially as described in Graham and Prevac (1991).

Transient transfections of H1299 cells were done with the pIN2 plasmid, also known as pCMV-p53. pIN2 was generated by insertion of the CMV-p53-SV40 poly A segment from Adp53 into pBluescript, this generating a plasmid containing the wild type 2.3 Kb p53 gene driven by a CMV promoter and regulated downstream by an SV40 poly A signal.

ITIC1 cells containing wild type p53 were generated using the LacSwitch system (Stratagene), which utilizes an IPTG inducible pair of plasmids. The p53 gene was cloned into the lac repressible plasmid pOPRSVICAT; the resulting construct referred to as pIN92. Another plasmid, p3'SS, encodes a constitutively active lac repressor gene. When pIN92 and p3'SS are co-transfected into a cell, the constitutive expression of the lac repressor prevents the expression of p53 by binding to lac operator sequences upstream of the transcription start site. The addition of IPTG inactivates the lac repressor by binding to it, thus allowing transcription of p53. Both plasmids were isolated and purified by conventional molecular biology techniques.

c. Production of Anti-Proliferative Factor in Cell Conditioned Media from Adp53 and Adβgal Infected H1299 Cells On day one H1299 cells were plated in T-75 flasks at a confluency of ~55% in high glucose DMEM containing 5% FBS. On day two the cells (~85% confluent) were infected with the Adp53 virus, the control virus containing the B-galactosidase gene instead of the p53 gene (Adβgal) or mock-infected with media, in 5 ml at a multiplicity of infection (MOI) of 5 or 20. The cells were infected for 3 hours and then the virus was removed by three washes with 10 ml of media and 10 ml of fresh media was put on the cells. The cells were left at 37° C./5%$CO_2$ for 72 hr. On day four the naive H1299 recipient cells were plated in 96-well plates, in triplicate wells for each sample, at ~19% confluency in 200 µl. On day five the cell conditioned media (CCM), also referred to as supernatant, was removed from the infected cells and cellular debris removed by centrifugation at 5000 rpm at 4° C. for 20 minutes, and the supernatant further fractionated through an Amicon Centriplus 100 molecular weight cutoff membrane. During the fractionation process, the remaining samples were kept on ice at 4° C. and all centrifugations were at 4° C. The samples were then warmed to room temperature prior to addition to the naive cells. The presence of infectious virus remaining in each fraction was determined by cytopathic effect (CPE) assay. CPE was observed with all unfractionated aliquots but not in any of the fractions obtained after passage through the 100 kd molecular weight cutoff membrane.

d. Production of Anti-Proliferative Factor in Cell Conditioned Media from pIN2 Transfected H1299 Cells On day one H1299 cells were seeded at a density of $2.5 \times 10^5$ cells/dish into a 60 mm dish. A total of one hundred dishes (50 dishes for each plasmid transfected) were seeded for pIN2 and p3'SS (plasmid used as a transfection control) transfection. On day two transient transfections were set up as follows: In a 12×75 mm sterile polystyrene tube 5 µg of pIN2 plasmid DNA was added to 295 µl of OptiMEM (Gibco-BRL). In a separate tube, 25 µl of Lipofectamine (Gibco-BRL) was added to 275 µl of OptiMEM. The two tubes were incubated at room temperature (20° C.) for 15 minutes. The contents of the DNA/OptiMEM tube were mixed with the contents of the Lipofectamine/OptiMEM tube and incubated at room temperature for 45 minutes. The 60 mm dishes containing $5 \times 10^5$ cells were washed once with OptiMEM and then a 2.4 ml aliquot of OptiMEM was added per dish. The entire transfection mixture (0.6 ml of the DNA/Lipofectamine mixture) was then added to a 60 mm dish. The dishes were incubated for 6 hours at 37° C. in 10% $CO_2$. After the incubation, the transfection mixture was removed, the cells were washed twice with DMEM containing 5% FBS (DMEM from Gibco-BRL and FBS from HyClone) media, and a 4 ml aliquot of DMEM/5% FBS was added per dish. The cells were incubated at 37° C. in 10% $CO_2$. On day four, 48 hours post-transfection, the media was removed from the 60 mm dishes, the cells were washed once with PBS (Gibco-BRL) and treated with 0.25% trypsin/EDTA (Gibco-BRL). Once detached, the trypsin was inactivated in an equal volume of DMEM/5% FBS, the cells were collected and pooled from the 60 mm dishes, and the cell density was determined. A total of 12 ml ($3 \times 10^6$ cells and DMEM/5% FBS) was aliquoted into T-75 flasks. The flasks were then incubated 24 hours at 37° C. in 10% $CO_2$.

e. Production of Anti-Proliferative Factor in Cell Conditioned Media from ITIC1 Cells The establishment of ITIC1 cells containing pIN92 (RSV-promoted p53 under control of Lac repressor) and p3'SS (plasmid expressing the Lac repressor) was performed as described in the transient-transfection section except that on day four the transfected cells were seeded into 100 mm dishes and 10 ml of double selection media (DMEM/5% FBS, 400 µg/ml neomycin, 250 µg/ml hygromycin) was added. On day 14, individual colonies were isolated by utilizing trypsin-saturated discs and subsequently transferred to 24-well plates containing 1 ml of double selection media per well. On day 21, the colonies were analyzed for their level of p53 upon IPTG-induction. A single colony was selected based on its low constitutive p53 levels and its high p53 levels upon IPTG-induction.

One day prior to assay for anti-proliferative activity, H1299 and ITIC1 cells were treated with trypsin/EDTA, inactivated in an equal volume of DMEM/5% FBS, pelleted by centrifugation and subsequently resuspended into DMEM/5% FBS. H1299 and ITIC1 cells were seeded into four T-75 flasks (two flasks for each cell line) at $3 \times 10^6$ cells per flask and DMEM/5% FBS media was added to give a total volume of 12 ml/flask. IPTG (final concentration of 5 mM) was added to one flask each of H1299 and ITIC1 cells and incubated for 24 hours at 37° C. in 10% $CO_2$, at which time the CCM is collected or frozen at −80° C.

f. Assay for Anti-Proliferative Activity

In general, naïve H1299 cells were seeded into 96-wells plates at a cell density of 500 cells /well in 100 µl and incubated for 24 hours at 37° C. in 10% $CO_2$. 100 µl aliquots of CCM were added to the wells in the 96-well plates. Tritiated thymidine was added to cells and allowed to incorporate for 15 hours prior to analysis. In some experiments, in order to include an 8 hour time point, the $^3$H-thymidine exposure time was reduced from 15 to 6 hours. Thus 6 hours prior to the time point of interest $^3$H-thymidine was added and the rest of the experiment was carried out as previously described. In addition to the 8 hour time point, 24, 48, 72 and 96 hour time points post-addition of CCM were also analyzed.

g. Growth Assay by Cell Counting

For cell growth measurements, cells were inoculated at densities of $1 \times 10^4$ cells in 12 well plates. Cells were trypsinized and counted using a hemocytometer. All studies were done in triplicate.

h. Tritiated Thymidine Incorporation Assay

Growth inhibition of cells after addition of cell conditioned medium containing the anti-proliferative factor was primarily measured by analysis of DNA synthesis. Briefly, a stock solution of 100 µCi/ml of $^3$H-thymidine (Amersham) was prepared by dilution into high glucose DMEM. $^3$H-thymidine to a final concentration of 1 µCi/ml was added to each well in 20 µl. The reaction was stopped 6 or 15 hours later by removal of supernatant from recipient cells. The cells were harvested by the addition of 100× trypsin/EDTA to each well for five minutes at room temperature. Cells were collected using a Packard Filtermate cell harvester following manufacturer's protocol and washed in distilled deionized water and methanol. Alternatively, the reaction was stopped by removing the supernatant from recipient cells and the cells were washed once with PBS+0.5 mM $MgCl_2$/1 mM $CaCl_2$ and 30 µl of lysis buffer (0.05% SDS/1 mM $MgCl_2$/1 mM $CaCl_2$) added. The cells were scraped, adsorbed onto Whatman filters and non-specific radioactivity was removed by washing with TCA. Filters were placed into 5 ml scintillant and counted in a gamma counter.

i. Stability Assays

Several assays were performed to assess the biological stability of the anti-proliferative activity observed in cell conditioned media in response to cellular stress.

Determination of the effects of pH on the biological activity present in cell conditioned media was measured by dialysis against buffers of different pH. CCM from IPTG-induced H1299 cells stably transfected with p53 was dialyzed against buffers from pH2 to pH12 at 4° C. overnight, using Spectro/Por CE Sterile Membranes or Sterile Dispo-Dialyzers. Buffer compositions were obtained from Buffers for pH and Metal Ion Control (1974). pH was quantitated using either pH paper or a pH meter. After dialysis of the CCM into buffers of varying pH, the pH was neutralized by dialysis back into DMEM/PBS. The resultant CCM was then sterilized by filtration through a 0.22 $\mu$M filter and 100 $\mu$l was added to naïve H1299 cells to look for retention of biological activity.

The effects of temperature on the biological activity of the anti-proliferative factor was also measured. Cell conditioned medium was subjected to long term storage at 4° C., –20° C. and –80° C. as well as multiple freeze/thaw cycles. CCM was also heated to 100° C. for 10 minutes in a boiling water bath. Post-treatment CCM was then assayed for anti-proliferative activity on naïve H41299 cells.

Cell conditioned medium was also treated with proteases and nucleases to analyze whether or not the anti-proliferative activity was mediated by molecules of nucleic acid or protein origin. CCM was treated with varying levels of benzonase, which hydrolyzes both single and double stranded nucleic acids into individual nucleotides. CCM was also treated with varying levels of trypsin, proteinase K, and pronase. Proteinase K, and pronase, which consists of a mixture of proteases, essentially reduces polypeptides into individual amino acids. Trypsin recognizes specific amino acid sequences and reduces proteins into short peptide fragments. The treated CCM was assayed for anti-proliferative activity against naïve H1299 cells, as previously described. The standard protocol for the use of these enzymes is well known to those of skill in the art.

j. Molecular Weight Fractionation

Crude fractionation of cell conditioned media was initially performed by centrifugation at 5000 rpm at 4° C. for 20 minutes to remove cellular debris. Further fractionation was done by passing the supernatant after centrifugation through molecular weight cutoff membranes (Amicon) ranging in size from 100 Kd to 3 Kd. Dialysis membranes retaining solutes of 2000 Da, 1000 Da and 500 Da were also used. In order to isolate and further characterize the anti-proliferative factor, 50 ml of <3000 Kd material derived from CCM collected from IPTG-induced ITIC1 cells was lyophilized overnight to complete dryness in a Labconco freeze drying system according to manufacturer's instructions. The lyophilized CCM was then resuspended into 2.0 ml of distilled water, resulting in a 25-fold concentration of the CCM. After resuspension, 300 $\mu$l of the concentrated CCM was size fractionated on a Pharmacia Biotech Superdex Peptide HR10/30 column with a molecular weight separation range of 100 to 7000 Da.

After the column was conditioned in 1× PBS, the aliquot of ITIC1 CCM was loaded onto the column and the fractions were eluted with 1× PBS. The absorbance at 280 nM and other wavelengths, and the conductivity were monitored. Fractions of 2.5 ml each were collected and sterile filtered by passage through a 0.22 $\mu$M sterile filter. Anti-proliferative activity was monitored by placing a 100 $\mu$l aliquot of each sterile fraction into a well of a 96-well plate containing naïve H1299 (initial confluency of 5%) cells and 100 $\mu$l of DMEM/5% FBS media. The extent of DNA synthesis inhibition was determined by $^3$H-thymidine incorporation assay at 48 hours post-addition of the fractions, as previously described.

EXAMPLE II

Growth Inhibitory Effects of Cell Conditioned Medium from Adp53 Infected H1299 Cells The inventors tested whether infection of H1299 cells with Adp53 and Ad$\beta$gal would induce the production of a factor that is secreted into cell conditioned medium, that when added to naïve cells, would result in growth inhibition of the cells.

H1299 human non-small lung carcinoma cells (p53 null) were infected with a recombinant adenovirus containing the wild type p53 gene at an MOI of either five or 20. After 72 hours, supernatant was collected from the cells, passed through a molecular weight cutoff membrane of 100 Kd to remove viral particles, and transferred onto naïve H1299 cells. Significant growth inhibition as measured by tritiated thymidine uptake was observed after 8, 29 and 53 hours of labeling, as compared to naïve H1299 cells treated with fresh media or media from uninfected H1299 cells (FIG. 1). Both an MOI of five and 20 were equally effective at induction of the anti-proliferative activity in CCM of infected cells. The absence of infectious adenovirus in the post C-100 fractions was confirmed by scoring for cytopathic effects on 293 cells.

Figure 2:
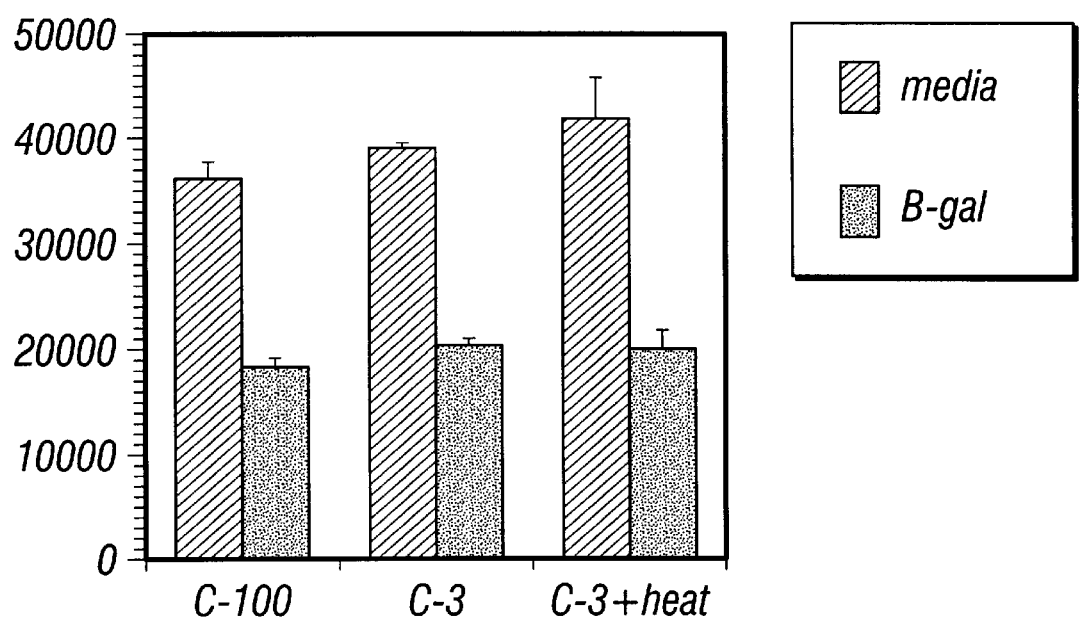
FIG. 2—Growth inhibition of naïve H1299 cells after treatment with fractionated cell conditioned medium from Adβgal infected H1299 cells. Naïve H1299 cells were plated into 96 well plates at a confluency of 5% and post C-100 ($1^{st}$ set), post C-3 ($2^{nd}$ set), or post C-3+ heat treated ($3^{rd}$ set) supernatant from uninfected ($1^{st}$ bar from left in each set) or Adβgal infected ($2^{nd}$ bar) H1299 cells was added. Cell growth was measured as $^3$H-thymidine incorporation at 19.25 hours.

As a control, H1299 cells were infected with Ad$\beta$gal at an MOI of 5 and the resultant CCM was assayed for anti-proliferative activity after passage through a molecular weight cutoff membrane of 100 Kd or 3 Kd, as well as treatment at 100° C. for 10 minutes. Surprisingly, significant growth inhibition of naïve H1299 cells was observed after all treatments and after 15 hours of labeling with $^3$H-thyimdine compared with cells that only received cell conditioned media from uninfected H1299 cells (FIG. 2). Thus it appears that infection of H1299 cells with an adenoviral vector encoding either a wild type p53 gene or a gene such as $\beta$-galactosidase results in the induction of a factor that is present in cell conditioned medium, and then when transferred to naïve tumor cells, is able to inhibit the growth of those cells. Additionally the factor that is exhibiting anti-proliferative activity is not p53, derived from p53, or induced by p53.

EXAMPLE III

Growth Inhibitory Effects of Cell Conditioned Medium from p53 Transfected H1299 Cells The inventors tested whether transfection of H1299 cells with plasmids encoding wild type p53 would induce the production of a factor that is secreted into cell conditioned medium, that when added to naïve cells, would result in growth inhibition of the cells.

H1299 cells were either transiently transfected with pIN2; or stably co-transfected with p3'SS and pIN92, establishing the ITIC1 cell line. Cell conditioned medium was collected from the transfected cells, pelleted to remove cellular debris, and transferred onto naïve H1299 cells.

Figure 3:
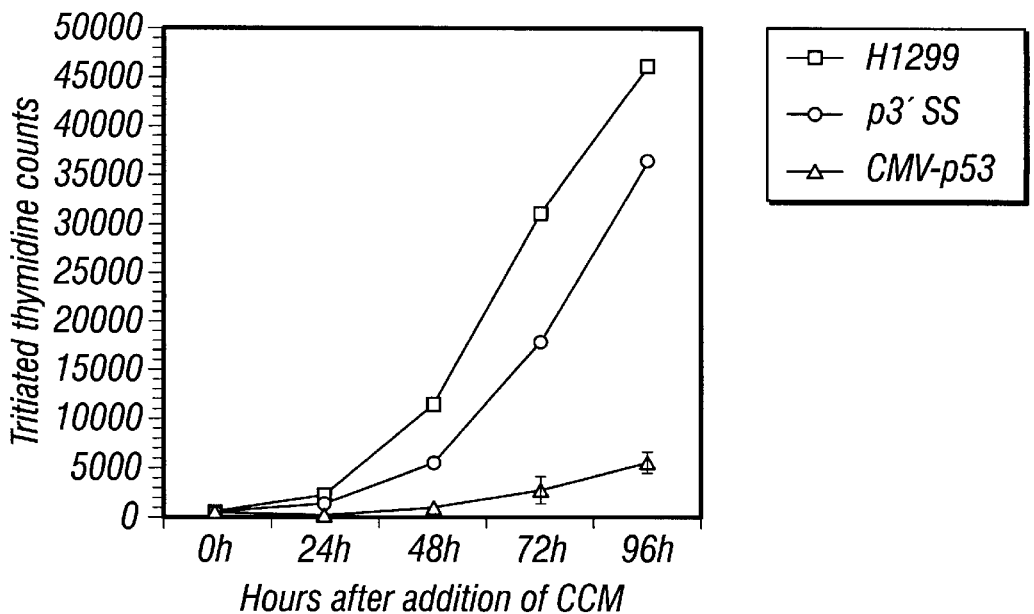
FIG. 3—Growth inhibition of naïve H1299 cells after treatment with supernatant from pIN2 transiently transfected H1299 cells. Naïve H1299 cells were seeded into 96 well plates at a confluency of approximately 5% and supernatant from untransfected (closed squares) H1299 cells, H1299 cells transiently transfected with control vector, p3'SS (open circles), or H1299 cells transiently transfected with pIN2 was added to each well. Cell growth was measured as $^3$H-thymidine incorporation at 24, 48, 72 and 96 hours.
Figure 4:
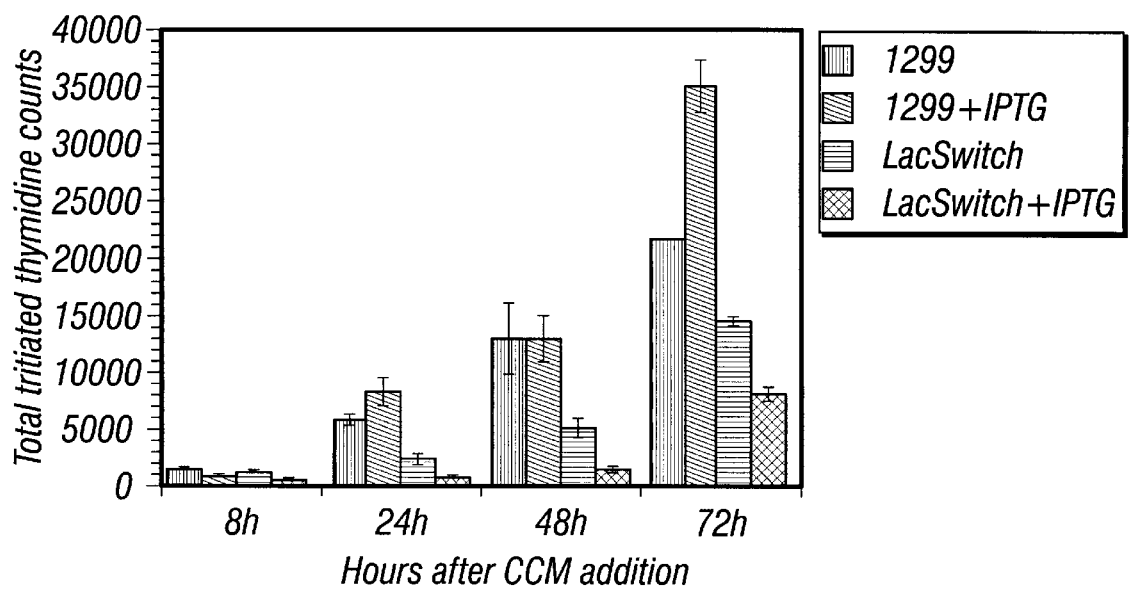
FIG. 4—Growth inhibition of naïve H1299 cells after treatment with supernatant from IPTG-induced ITIC1 cells. Naïve H1299 cells were seeded into 96 well plates at a confluency of approximately 5% and supernatant from untreated (1st bar from left) or IPTG-treated ($2^{nd}$ bar) H1299 cells; or untreated ($3^{rd}$ bar), or IPTG-treated ($4^{th}$ bar) ITIC1 cells was added. Cell growth was measured as $^3$H-thymidine incorporation at 8, 24, 48, and 72 hours.

Inhibition of cell growth as measured by tritiated thymidine incorporation was observed when cell conditioned medium for pIN2 transient transfected H1299 cells was added to naïve H1299 cells, in contrast to supernatant from H1299 cells transiently transfected with a control vector, p3'SS (FIG. 3). The growth inhibitory effect increased significantly between 48 and 96 hours after addition of the CCM to the naïve cells. Similarly, addition of CCM from IPTG-induced ITIC1 cells resulted in significant growth inhibition of naïve H1299 cells that increased over a time period of eight to 72 hours (FIG. 4) In contrast, addition of CCM from either IPTG-treated or untreated H1299 cells to naive H1299 cells did not affect the proliferation of the cells. Surprisingly, cell conditioned medium from IPTG-untreated ITIC1 cells resulted in partial growth inhibition.

Leakiness of the lac repressible p53 expression is unlikely to play a role in the induction of this activity as ITIC1 clones were chosen that exhibited very low levels of p53 expression when not induced by p53. However, addition of foreign genetic material into cells that constitutively expresses a protein not normally found in cells in large quantities, may activate or induce cellular factors that are released into the surrounding medium. Such factors may have growth inhibitory effects on naïve cells.

EXAMPLE IV

Effects of Anti-Proliferative Factor on Fibroblasts and Tumor Cells of Varying p53 Phenotype The inventors tested the effects of cell conditioned media from IPTG-induced ITIC1 cells on the growth of fibroblasts and non-small cell lung carcinoma cells of varying p53 status.

Figure 5:
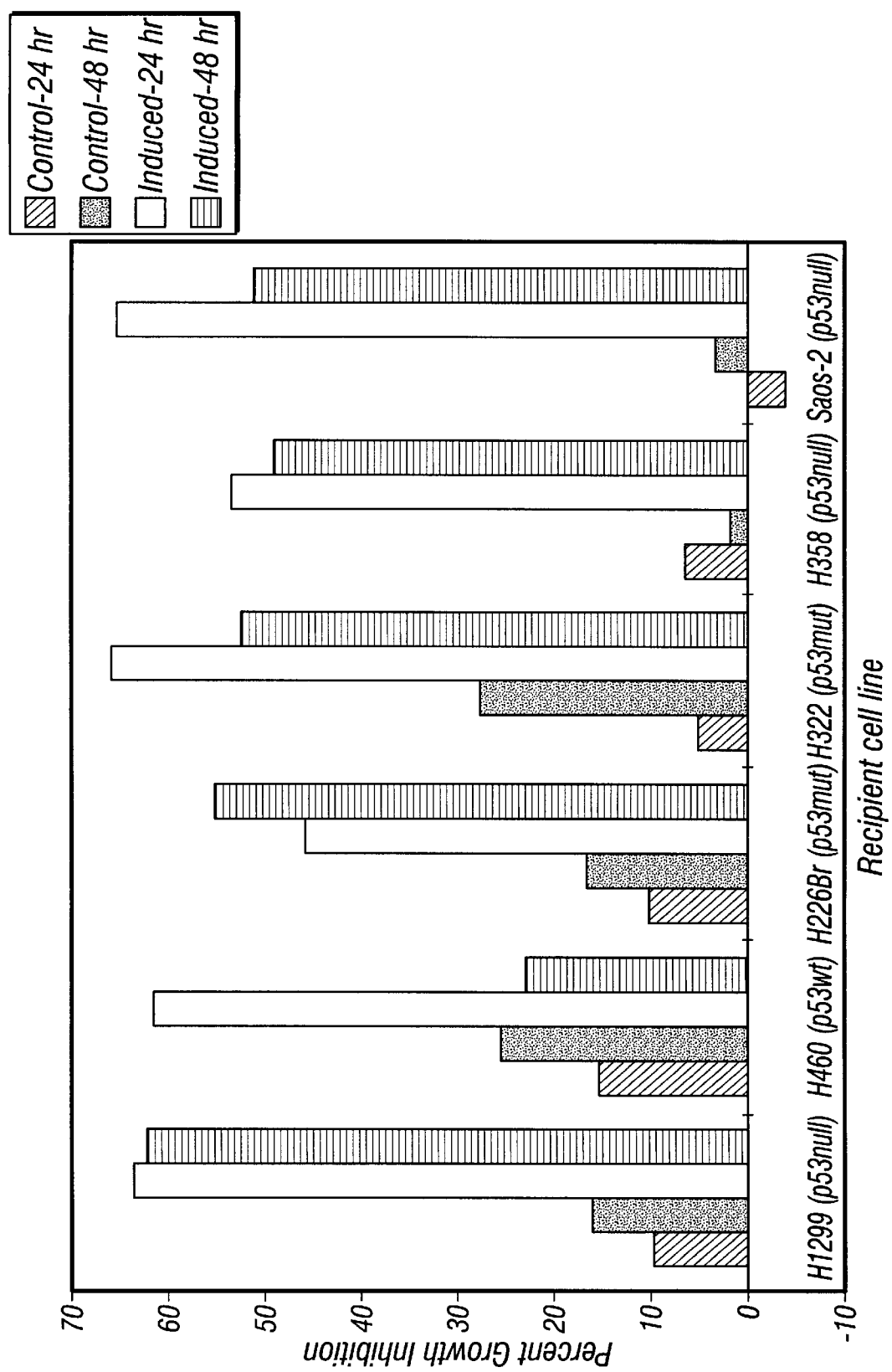
FIG. 5—Growth inhibition of tumor cells with varying p53 phenotypes after incubation with supernatant from IPTG-induced ITIC1 cells. Supernatant from H1299 cells after 24 ($1^{st}$ bar from left), or 48 ($2^{nd}$ bar) hours, or IPTG-induced ITIC1 cells after 24 ($3^{rd}$ bar) or 48 ($4^{th}$ bar) hours was added to naïve tumor cells seeded at a confluency of 5%. Non-small cell lung carcinoma cell lines tested were: H1299 (p53 null), H460 (p53 wt), H226Br (p53 mutant), H322 (p53 mutant), H358 (p53 null) and Saos-2 (p53 null). Cell growth was measured by $^3$H-thymidine incorporation at 24 and 48 hours and expressed as percent growth inhibition.

Growth inhibitory effects of CCM as tested against the following cell lines: H1299 (p53 null), H460 (p53 wt), H226Br (p53 mutant), H322 (p53 mutant), H358 (p53 null), and Saos-2 (p53 null). In all cell lines tested, CCM from IPTG-induced ITIC1 cells inhibited cell growth after 24 hours (FIG. 5) as compared to CCM from control IPTG-treated H1299 cells. Similar results were observed at 48 hours post addition of the CCM onto all of the naïve cells tested, with the exception of H460 cells, which naturally express wild type p53. Thus it appears that the anti-proliferative activity present in CCM efficiently inhibits the growth of tumor cells for 24 hours regardless of their p53 status, and for at least 48 hours in cells with either deleted or mutant p53.

Figure 6:
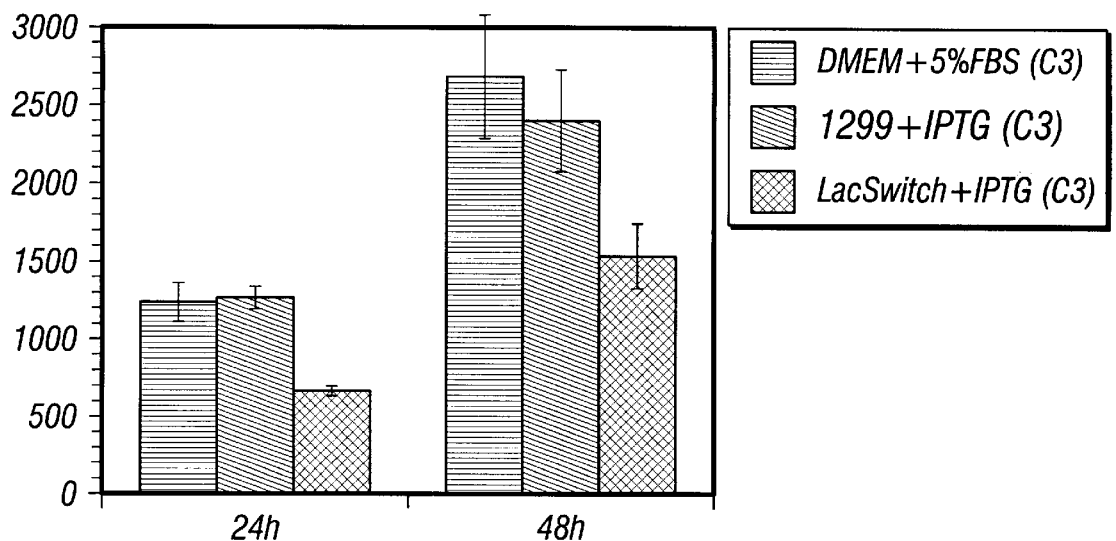
FIG. 6—Growth inhibition of fibroblasts after incubation with cell conditioned medium from IPTG-induced ITIC1 cells. Supernatant was collected and passed through a 3000 MW cutoff membrane. Fractionated fresh media from ($1^{st}$ bar from left in each set), IPTG treated H1299 cells ($2^{nd}$ bar), or IPTG treated ITIC1 cells was added to naïve human foreskin fibroblasts at a confluency of $1.5 \times 10^3$ cells/ml. Cell growth was measured by $^3$H-thymidine incorporation at 24 and 48 hours.

Studies with fibroblasts showed similar growth inhibition effects (FIG. 6). Significant but reduced levels of growth inhibition were observed after addition of CCM from IPTG-induced ITIC1 cells at both 24 and 48 hours compared to treatment with media alone or parental H1299 cells treated with IPTG. This suggests that the anti-proliferative activity present in CCM does not only inhibit growth of tumor cells but non-malignant cells as well, and thus may be useful for the treatment of hyper-proliferative disorders.

EXAMPLE V

Molecular Weight Fractionation of Cell Conditioned Medium

The inventors fractionated the cell conditioned medium from IPTG induced ITIC1 cells using molecular weight cutoff membranes to further isolate the factor responsible for effecting anti-proliferative activity.

Figure 7:
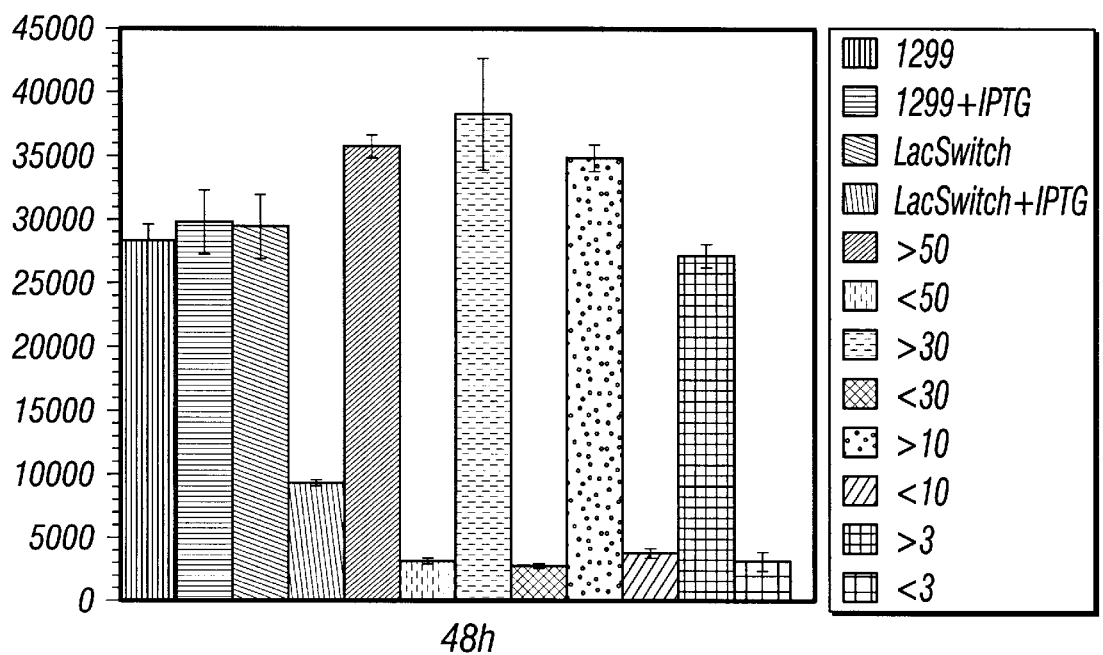
FIG. 7—Growth inhibition of naïve H1299 cells after crude molecular weight fractionation of cell conditioned medium. Naïve H1299 cells were seeded onto 96 well plates at a confluency of 5% and treated with unfractionated supernatant from control cells. Controls were CCM from either untreated ($1^{st}$ bar from left) or IPTG treated ($2^{nd}$ bar) H1299 cells and untreated ($3^{rd}$ bar) or IPTG treated ($4^{th}$ bar) ITIC1 cells. Similarly, fractionated supernatant from IPTG-induced ITIC1 cells using molecular weight cutoff membranes that isolated fractions of >50 MW ($5^{th}$ bar), <50 MW ($6^{th}$ bar), >30 MW ($7^{th}$ bar), <30 MW ($8^{th}$ bar), >10 MW ($9^{th}$ bar), <10 MW ($10^{th}$ bar), >3 MW ($11^{th}$ bar), and <3 MW ($12^{th}$ bar) were added to naïve H1299 cells. Cell growth was measured as $^3$H-thymidine incorporation at 48 hours.
Figure 8:
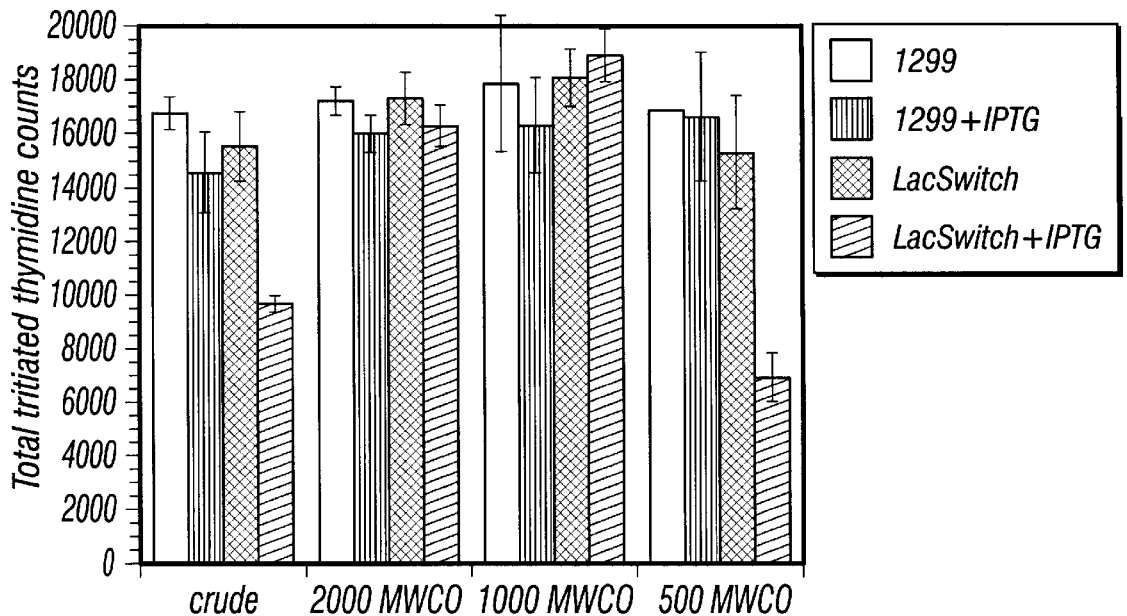
FIG. 8—Growth inhibition of naïve H1299 cells after crude molecular weight fractionation by dialysis of cell conditioned medium. Naïve H1299 cells were seeded onto 96 well plates at a confluency of 5% and supernatant from untreated ($1^{st}$ bar from left in each set), IPTG-treated ($2^{nd}$ bar) H1299 cells, untreated ($3^{rd}$ bar), or IPTG-treated ($4^{th}$ bar) ITIC1 cells was added. The supernatant was either unfractionated ($1^{st}$ set), or separated into fractions of >2000 MW ($2^{nd}$ set), >1000 MW ($3^{rd}$ set) or >500 MW ($4^{th}$ set). Cell growth was measured as $^3$H-thymidine incorporation at 48 hours.

ITIC1 cells were treated with IPTG and twenty-four hours later, CCM was collected and passed through molecular weight cutoff membranes of 50 Kd, 30 Kd, 10 Kd and 3 Kd. Both material that was retained by the membrane and material that passed through each membrane was tested for the ability to inhibit the growth of naïve H1299 cells. Unfractionated and all breakthrough fractions retained the ability to inhibit cell growth (FIG. 7). Conversely, material retained by each membrane as well as CCM from control IPTG untreated ITIC1 cells and parental H1299 cells did not inhibit growth. Further fractionation using dialysis membranes with molecular weight cutoffs of approximately 2000 Da, 1000 Da, and 500 Da was performed. Anti-proliferative activity was lost in both the 2000 Da and 1000 Da fractions, but was retained in the fraction that contained molecules of approximately greater than 500 Da. Thus, it appears that the one factor responsible for anti-proliferative activity is a small molecule ranging in size from approximately 500 Da and 1000 Da. Because of non-uniform pore size in molecular weight cutoff membranes, the actual size of the factor responsible for anti-proliferative activity may be significantly larger or smaller than the range currently identified.

EXAMPLE VI

Effects of Protease and Nuclease Treatment on Anti-Proliferative Activity

Figure 9:
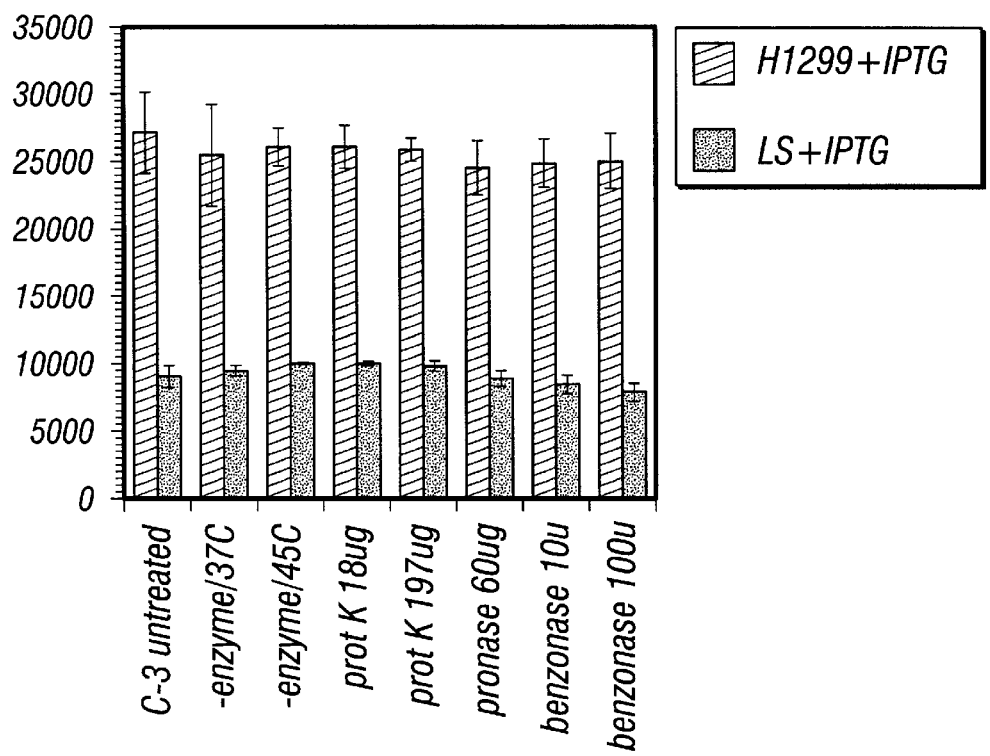
FIG. 9—Growth inhibition of naïve H1299 cells after incubation with protease- or nuclease-treated CCM from IPTG-induced ITIC1 cells. Naïve H1299 cells were seeded into wells of a 96 well plate at a confluency of 5% and supernatant from uninduced ($1^{st}$ bar from left) or IPTG-induced ($2^{nd}$ bar) ITIC1 cells was added. Before addition of the supernatant, it was fractionated through a 3000 MW cutoff membrane and either untreated (1st set), incubated at 37° C. ($2^{nd}$ set), incubated at 45° C. ($3^{rd}$ set), treated with 18 μg proteinase K ($4^{th}$ set), 197 μg proteinase K ($5^{th}$ set), 60 μg pronase ($6^{th}$ set), 10 μg benzonase ($7^{th}$ set) or 100 μg benzonase ($8^{th}$ set). Cell growth was measured as $^3$H-thymidine incorporation at 48 hours.

The inventors tested the effects of protease and nuclease treatment on the anti-proliferative activity present in cell conditioned medium from IPTG-induced ITIC1 cells. Cell conditioned medium was collected from ITIC1 cells after treatment with IPTG and passed through a 3 Kd molecular weight cutoff membrane. The resulting breakthru was then either heat treated at 37° C. or 45° C., or treated with proteinase K, pronase, or benzonase. For all treatments, anti-proliferative activity was observed when the fractionated, treated CCM was added to naïve H1299 cells (FIG. 9). Cell conditioned medium collected from IPTG-treated parental H1299 cells and subjected to the same heat and enzyme treatments did not have any growth inhibitory effect on the growth of naïve H1299 cells. Control experiments showed that the enzyme preparations were biologically active and reduced both protein and DNA samples to undetectable levels. Thus is would appear that the factor responsible for the anti-proliferative activity in CCM is unlikely to be of protein or nucleic acid origin, since all enzyme treatments should have completely hydrolyzed the macromolecules into individual amino acids or nucleotides.

EXAMPLE VII

Anti-Proliferative Effects of a Factor Present in CCM on Endothelial Cells

The inventors tested the anti-proliferative activity present in cell-conditioned media (CCM) on the growth of normal endothelial cells. As previously described in the preceding examples, the CCM was obtained either from ITIC1 cells, which are H1299 non-small cell lung cancer cells stably transfected with an inducible vector system expressing wild-type p53, or from H1299 cells infected with Adp53, a recombinant adenovirus containing the wild-type p53 gene under the control of a CMV IE promoter and a SV40 poly-adenylation signal. The endothelial cells used in these studies were HUVEC (human umbilical vein endothelial cells), FBHE (fetal bovine heart endothelial), and EJG (bovine adrenal medulla endothelial) cells. The HUVEC cells were obtained from Clonetics(r) Corporation, San Diego, Calif. and the FBHE and EJG cells were obtained from ATCC (American Type Culture Collection), Gaithersburg, Md.

In general, endothelial cells were plated in 96-well plates at a cell density of 1000 cells/well in 100 ml of media at 37° C. in 5% $CO_2$. For the HUVEC cells, the plates were pre-coated with 0.2% gelatin to aid in cell attachment. After 24 hours, 100 ml aliquots of CCM were added to the wells of the 96-well plates. After 8 hours of incubation with the CCM, 3H-thymidine was added to the wells and at 24 hours post-addition of the CCM, the cells were harvested and the rate of DNA synthesis monitored by standard tritiated thymidine assay (see Example I for details).

Figure 10:
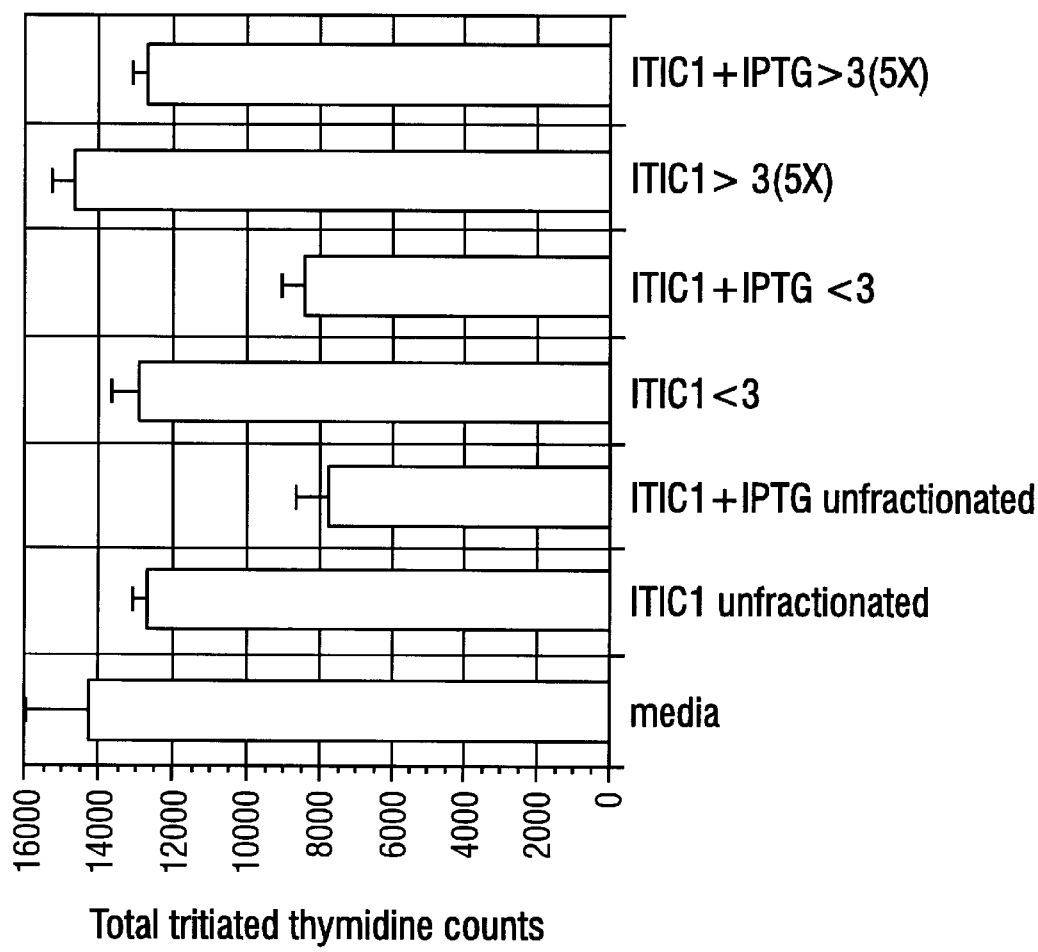
FIG. 10—Growth inhibition of naïve HUVEC cells after addition of CCM from IPTG-induced ITIC1 cells. Naïve HUVEC cells were seeded into wells of a 96-well plate at a concentration of 1000 cells/well. CCM was collected from ITIC1 cells that were either uninduced or IPTG-induced and a portion of the CCM was subsequently fractionated over a 3 kD molecular weight cutoff membrane; the remainder was left unfractionated. CCM from unfractionated uninduced cells (2nd bar from left), unfractionated IPTG-induced cells (3rd bar), <3 kD fraction from uninduced cells (4th bar), <3 kD fraction from IPTG-induced cells (5th bar), >3 kD fraction (5-fold concentrated) from uninduced cells (6th bar) and >3 kD fraction (5-fold concentrated) from IPTG-induced cells (7th bar) was added to the HUVEC cells. Growth inhibition was measured as a function of tritiated thymidine incorporation over time. A negative control of media only was also used (1st bar). See Example VII for experimental details.
Figure 11:
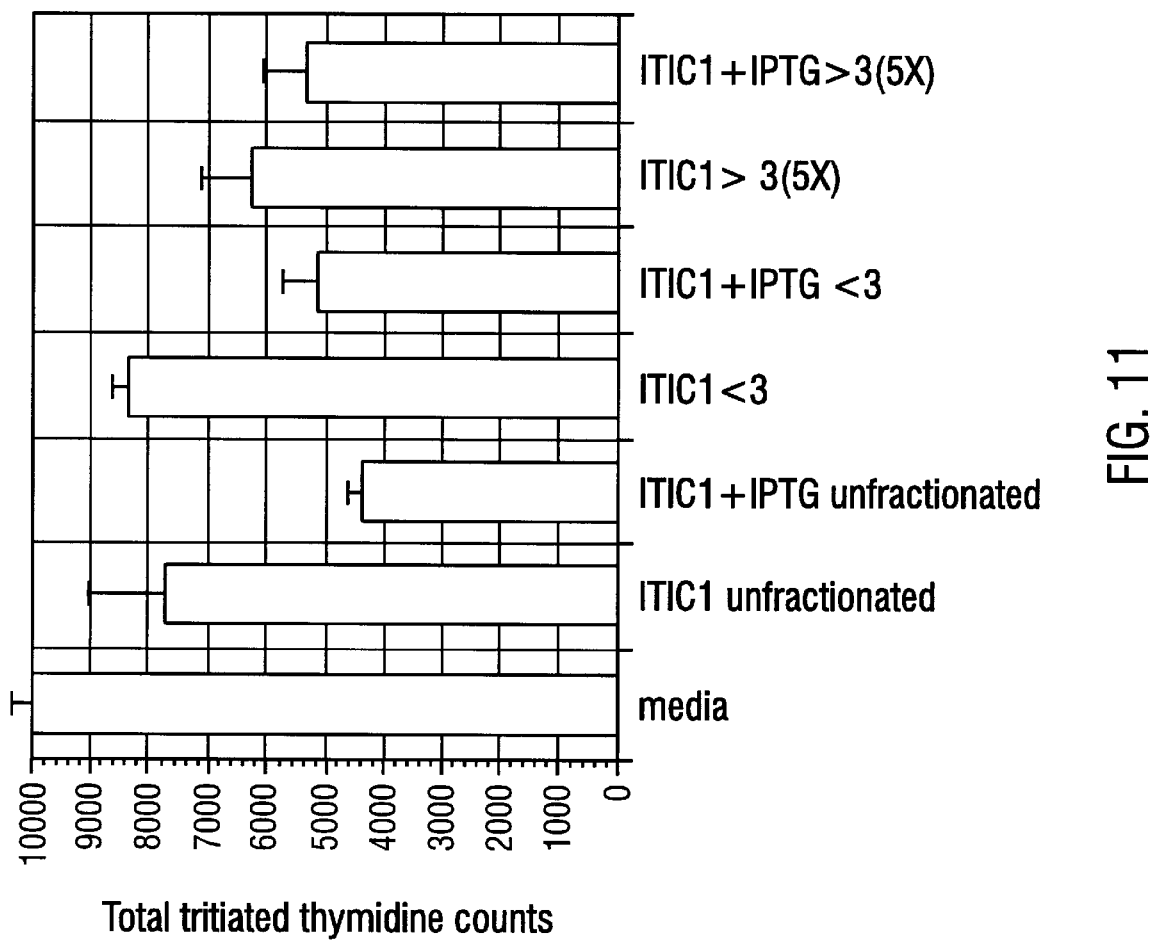
FIG. 11—Growth inhibition of naïve FBHE cells after addition of CCM from IPTG-induced ITIC1 cells. Naïve FBHE cells were seeded into wells of a 96-well plate at a concentration of 1000 cells/well. CCM was collected from ITIC1 cells that were either uninduced or IPTG-induced and subsequently fractionated over a 3 kD molecular weight cutoff membrane. CCM from unfractionated uninduced cells (2nd bar from left), unfractionated IPTG-induced cells (3rd bar), <3 kD fraction from uninduced cells (4th bar), <3 kD fraction from IPTG-induced cells (5th bar), >3 kD fraction (5-fold concentrated) from uninduced cells (6th bar) and >3 kD fraction (5-fold concentrated) from IPTG-induced cells (7th bar) was added to the FBHE cells. Growth inhibition was measured as a function of tritiated thymidine incorporation over time. A negative control of media only was also used (1st bar). See Example VII for experimental details.

ITIC1 cells were treated with IPTG and 24 hours later, CCM was collected and a portion passed through a molecular weight cutoff membrane of 3 kD. Naïve HUVEC cells were then treated with either uninduced unfractionated CCM, induced unfractionated CCM, uninduced fractionated CCM, or induced fractionated CCM. As can be seen in FIG. 10, growth as measured by DNA synthesis of HUVEC cells either mock treated with media only, or with uninduced CCM was not affected by the CCM. In contrast, those cells treated with both the unfractionated and fractionated CCM that was collected from IPTG-induced ITIC1 cells significantly reduced the rate of DNA synthesis of the HUVEC cells. In the greater than 3 kD fractions, the CCM was concentrated five-fold to see an effect on DNA synthesis relative to that obtained similarly with concentrated CCM from the uninduced cells. Similar results were obtained when FBHE cells were treated with the ITIC1 CCM (FIG. 11), although these cells did not show a significant difference in proliferation between treatments with the <3 kD fractions.

Figure 12:
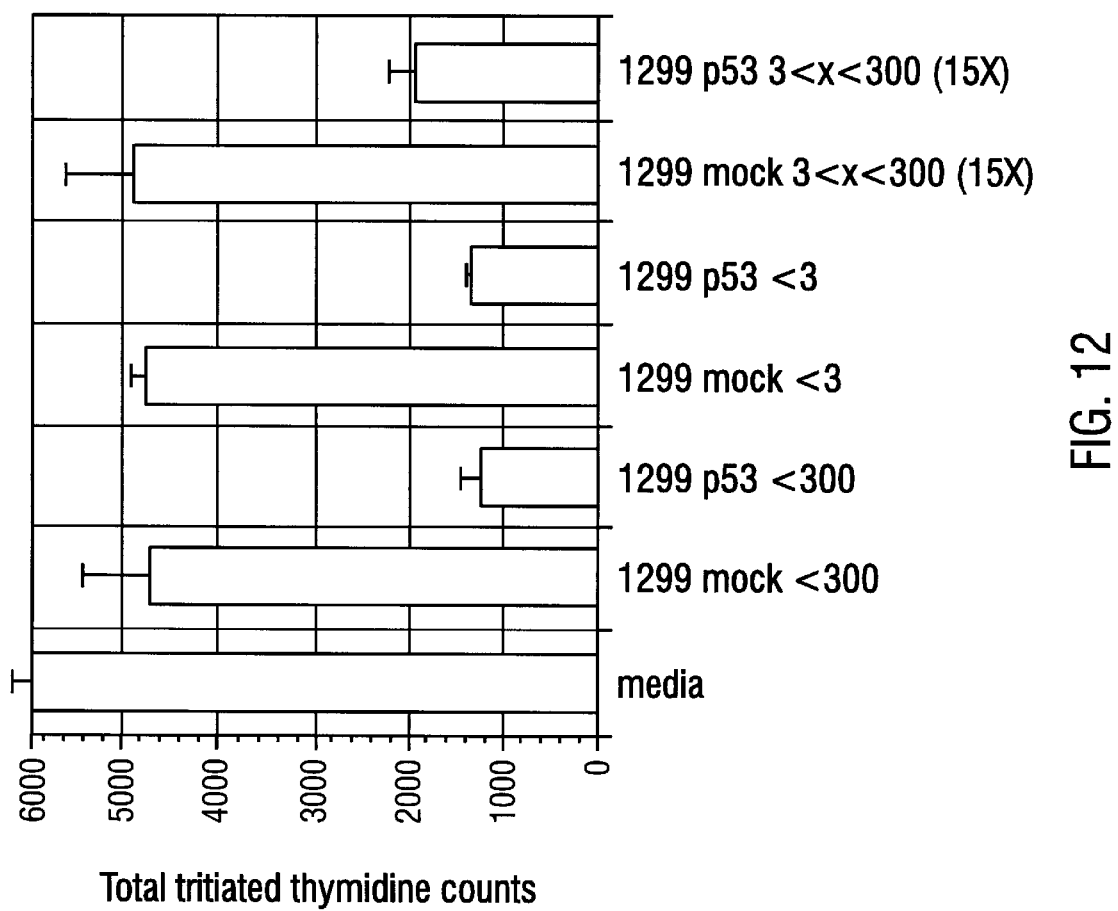
FIG. 12—Growth inhibition of naïve HUVEC cells after addition of CCM from Adp53-transduced H1299 cells. Naïve HUVEC cells were seeded into wells of a 96-well plate at a concentration of 1000 cells/well. CCM was collected from H1299 cells that were either mock-transduced or transduced with Adp53, and the CCM was then fractionated over a 300 kD and/or a 3 kD molecular weight cutoff membrane. The naïve HUVEC cells were then treated with media only (1st bar from left), mock-transduced CCM of <300 kD (2nd bar), Adp53-transduced CCM of <300 kD (3rd bar), mock-transduced CCM of <3 kD (4th bar), Adp53-transduced CCM of <3 kD (5th bar), 15-fold concentrated mock-transduced CCM of >3 but <300 kD (6th bar), or 15-fold concentrated Adp53-transduced CCM of >3 but <300 kD (7th bar). See Example VII for experimental details.
Figure 13:
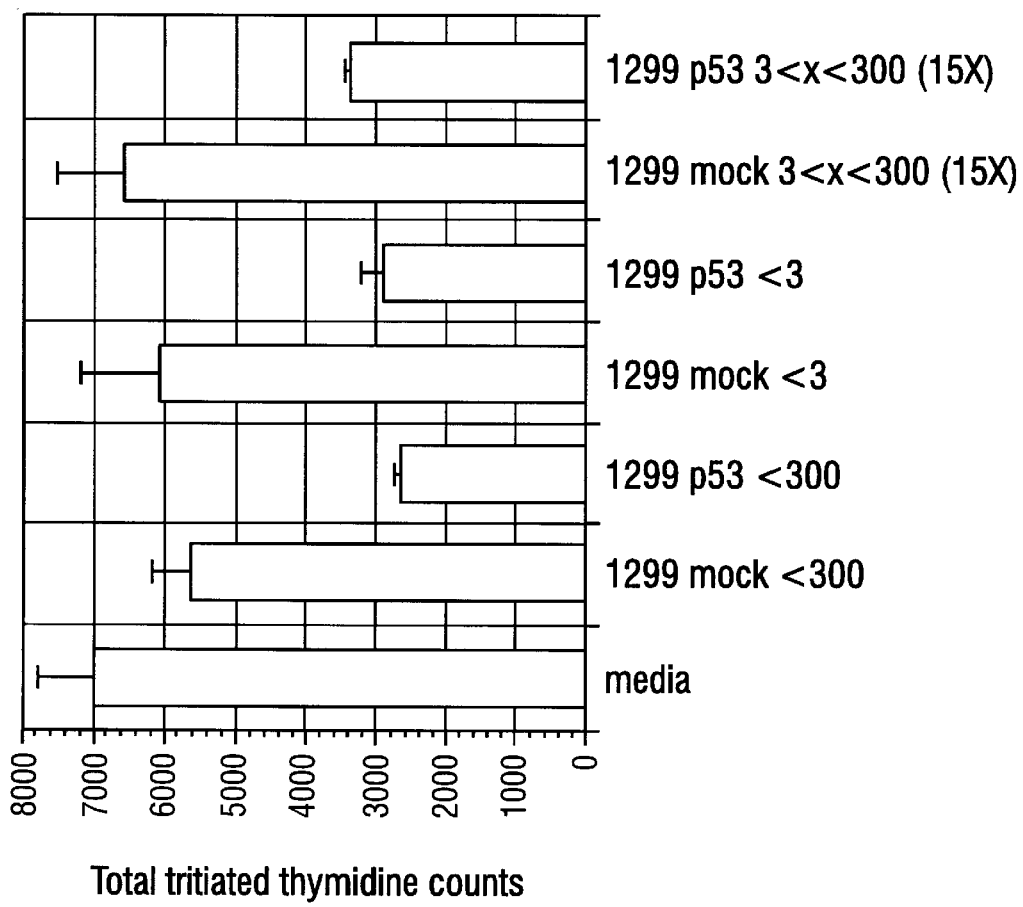
FIG. 13.—Growth inhibition of naïve FBHE cells after addition of CCM from Adp53-transduced H1299 cells. Naïve FBHE cells were seeded into wells of a 96-well plate at a concentration of 1000 cells/well. CCM was collected from H1299 cells that were either mock-transduced or transduced with Adp53, and the CCM was then fractionated over a 300 kD and/or a 3 kD molecular weight cutoff membrane. The naïve FBHE cells were then treated with media only (1st bar from left), mock-transduced CCM of <300 kD (2nd bar), Adp53-transduced CCM of <300 kD (3rd bar), mock-transduced CCM of <3 kD (4th bar), or Adp53-transduced CCM of <3 kD (5th bar), 15-fold concentrated mock-transduced CCM of >3 but <300 kD (6th bar), or 15-fold concentrated Adp53-transduced CCM of >3 but <300 kD (7th bar). See Example VII for experimental details.
Figure 14:
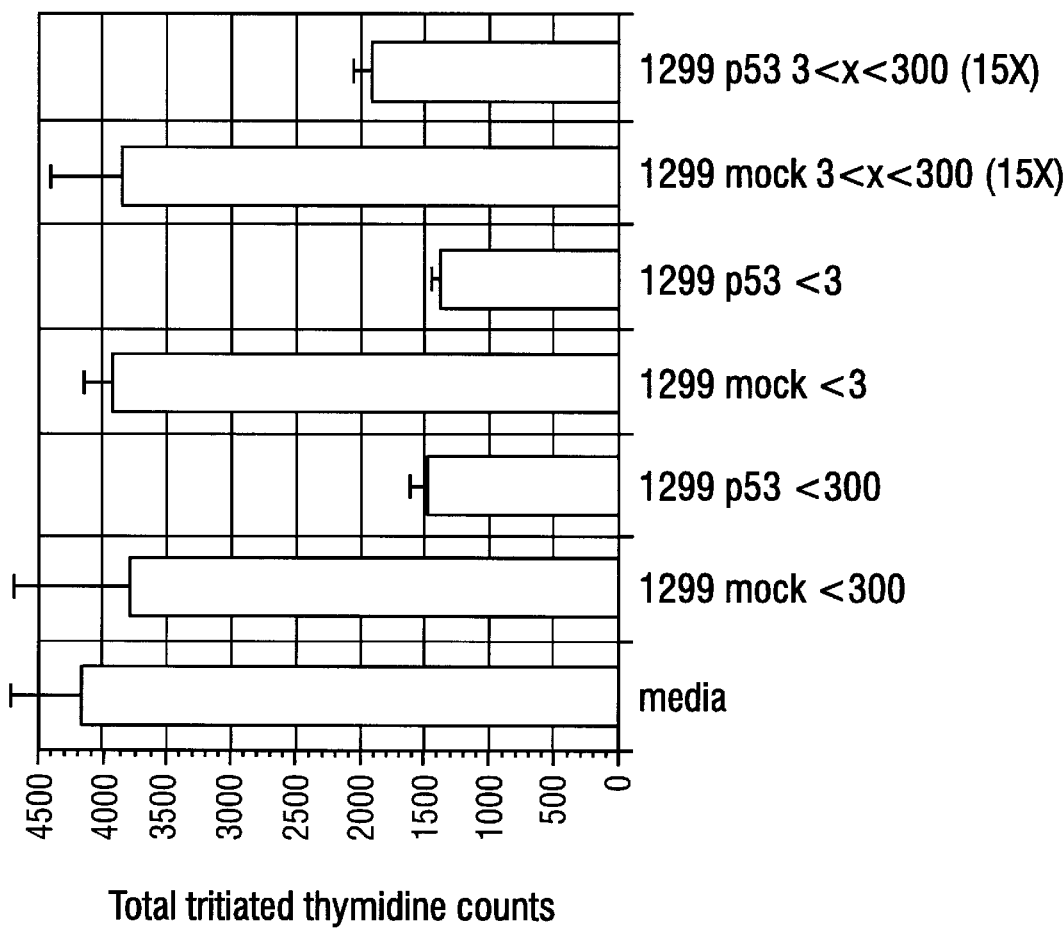
FIG. 14—Growth inhibition of naïve EJG cells after addition of CCM from Adp53-transduced H1299 cells. Naïve EJG cells were seeded into wells of a 96-well plate at a concentration of 1000 cells/well. CCM was collected from H1299 cells that were either mock-transduced or transduced with Adp53, and the CCM was then fractionated over a 300 kD and/or a 3 kD molecular weight cutoff membrane. The naïve EJG cells were then treated with media only (1st bar from left), mock-transduced CCM of <300 kD (2nd bar), Adp53-transduced CCM of <300 kD (3rd bar), mock-transduced CCM of <3 kD (4th bar), or Adp53-transduced CCM of <3 kD (5th bar), 15-fold concentrated mock-transduced CCM of >3 but <300 kD (6th bar), or 15-fold concentrated Adp53-transduced CCM of >3 but <300 kD (7th bar). See Example VII for experimental details.

H1299 cells were either mock-transduced or transduced with 10 MOI Adp53 and CCM was collected 24 hours later. The CCM was then fractionated through a 300 kD to remove virus and then through a 3 kD molecular weight cutoff membrane, and added to plated endothelial cells as described above. CCM from Adp53-transduced H1299 cells significantly reduced the level of DNA synthesis of naïve HUVEC (FIG. 12), FBHE (FIG. 13), and EJG (FIG. 14) cells, whereas CCM from mock-transduced H1299 cells had little or no effect on the same cells when compared to cells treated only with media. In each of the types of endothelial cell lines treated, there was anti-proliferative activity present in both the <3 kD fraction the 3<x<300 kD fraction, and the <300 kD fraction, thus indicating the likelihood that there is more than one factor of different sizes present in the CCM that exhibit anti-proliferative activity or perhaps a multimer of the smaller factor.

Thus, it is evident that CCM from both cells stably transfected with wild-type p53 gene and cells transduced with a recombinant adenovirus containing the wild-type p53 gene induce the production or secretion of a factor that has anti-proliferative activity against not only transformed cells, but also against normal endothelial cells and may play a significant role in inhibiting angiogenesis. Angiogenesis, the formation of new capillaries, plays a vital role in tumor formation and progression. The new blood vessels supply the tumor with nutrients which allows the tumor to grow but also provide a route for tumor cells to enter the bloodstream and metastasize to distant sites from the primary tumor. Angiogenesis is also important in normal functions such as wound healing, embryogenesis and in the reproductive system which explains why angiogenic and anti-angiogenic factors can be found within normal tissues as well as cancerous.

p53 appears to play a role in angiogenesis. Wild-type p53 has been shown to affect neovascularization in breast, brain, and connective tissue (Dameron et al., 1994). In normal human fibroblasts or fibroblasts from Li-Fraumeni patients with one wild-type p53 allele, a high level of the anti-angiogenic factor, thrombospondin-1 (TSP-1), is seen. When the wild-type p53 allele is lost during immortalization of the Li Fraumeni fibroblasts, the level of TSP-1 secretion drops dramatically. In addition, CCM from fibroblasts that have wild-type p53 prevents neovascularization in rat corneas and endothelial cell migration whereas CCM from fibroblasts which has lost p53 is unable to inhibit angiogenesis in vivo and in vitro.

VEGF (vascular endothelial growth factor), an angiogenic molecule which binds exclusively to endothelial cells and promotes their proliferation, is also affected by p53. In the Li Fraumeni fibroblasts, the loss of p53 causes the increase of VEGF production (Bouck, 1996). In addition, wild-type p53 has been shown to suppress basal VEGF transcription by an unknown mechanism (Mukhopadhyay et al., 1995).

The introduction of wild-type p53 into p53 mutant or null glioblastoma and breast cancer cells has been found to create an anti-angiogenic response (Van Meir et al., 1994). When wild-type p53 was introduced into the human glioblastoma cell line, LN-Z308 (p53 null), the secretion of an angiogenic inhibitor, GD-AIF, was discovered. CCM was collected in serum free media and concentrated approximately 20 times using a 3 kD cutoff. CCM from cells transfected with wild-type p53 caused the inhibition of endothelial cell migration in vitro and also prevented the neovascularization in rat corneas in vivo. This factor was found to be specific to p53, rather than mere cell cycle arrest since the addition of cell cycle inhibitors (aphidicolin, nocodazol and hydroxyurea) did not result in the secretion of the inhibitor. Thus far, the characterization of GD-AIF is limited. Preliminary data suggests that GD-AIF is greater than 100 kD, labile when treated with pronase of basic pH (12.3), stable when heated to 100° C. for 10 minutes and does not bind heparin.

Introduction of wild-type p53 into breast cancer cells results in the production of TSP-1 (Volpert et al., 1995). BT549 breast cancer cells with mutant p53 were infected with a retroviral vector expressing wild-type p53 and their CCM was tested for the ability to stimulate the migration of capillary endothelial cells and induce neovascularization in the rat cornea. CCM was collected in serum free media and concentrated using a 10 kD cutoff membrane. CCM from subclones expressing wild-type p53 were not angiogenic in vitro or in vivo while the CCM from the parental cell line was potently angiogenic. CCM from subclones was also able to inhibit migration induced by medium from the parental line and by the angiogenic factor, bFGF. When the CCM was incubated with antibodies to TSP-1, this inhibitory activity was lost.

Due to the increasing amount of information regarding p53 and its relationship to angiogenesis, it is possible that the bystander effect seen in gene therapy using wild-type p53 is due to the production or secretion of an anti-angiogenic factor which causes the tumor to lose its supply of nutrients and growth factors. Therefore, the role of angiogenesis should be explored in trying to understand and explain the "bystander effect." Thus, the studies described herein by the inventors have important implications for the use of an anti-proliferative factor or factors in treating cellular hyper-proliferative disorders such as cancer and abnormal proliferation of normal cells such as observed in restenosis.

EXAMPLE VIII

In Vivo Tumorigenicity Studies of Tumor Cells Pretreated with CCM Comprising an Anti-Proliferative Activity Further characterization of the anti-proliferative activity observed in the in vitro studies on tumor cells can be extended by in vivo studies on tumorigenicity and suppression of the growth of established tumors. Tumorigenicity experiments will be performed in Holland nude mice. CCM is collected from both H1299 cells (as a negative control) and ITIC1 cells induced with 5 mM IPTG, and then either unfractionated or fractionated over molecular weight cutoff membranes that separate molecules ranging in size from 3 kD to 300 kD. To test for anti-proliferative activity of the preparation, the CCM will be tested in vitro on naïve H1299 cells, as described in previous examples. After confirmation of anti-proliferative activity in vitro, naïve tumor cells will be exposed to the CCM for a period of time each day for a period of days. Any type of proliferating cell may be used in these studies, although the inventors contemplate using lung, breast, prostate, colon, squamous cell carcinoma, bladder, pancreatic, glioblastoma and melanoma tumor cells.

Initial experiments will be done with NSCLC cell lines, including but not limited to H1299, H358, H322 and H460. The time period for incubation of the tumor cells each day may be from 4 hour to 18 hours, although more preferably between 6 and 12 hours, and most preferably 8 hours. The number of days prior to implantation that the cells will be exposed to the CCM may be from 1 to 7 days, more preferably from 1 to 2 days, and most preferably for 1 day. After exposure of the tumor cells to the CCM, the cells will be implanted subcutaneously into the flanks of nude mice at a concentration of between $1\times10^3$ to $1\times10^{10}$ cells/mouse, but most preferably at a concentration of $2\times10^6$ cells/mouse. The mice will be monitored for tumor growth over a period of 60 days, and tumor size measured daily as soon as tumor growth is visible. Some tumors may be excised and analyzed microscopically and molecularly for evidence of growth suppression and apoptosis.

H. References

The following references, to the extent that they provide exemplary procedural or other details supplementary to those set forth herein, are specifically incorporated herein by reference:

Abbondanzo et al., *Breast Cancer Res. Treat.*, 16:182(#151), 1990.

Allred et al., *Breast Cancer Res. Treat.*, 16:182(#149), 1990.

American Cancer Society, Cancer Response System, Document #447058.

Antibodies. A Laboratory Manual, Cold Spring Harbour Laboratory, 1988.

Baichwal and Sugden, "Vectors for gene transfer derived from animal DNA viruses: Transient and stable expression of transferred genes," In: Kucherlapati R, ed. Gene Transfer. New York: Plenum Press, pp. 117–148, 1986.

Belani, "Multimodality management of regionally advanced non-small-cell lung cancer," *Seminars in Onocology*, 20(4): 302–14, 1993.

Benvenisty and Neshif, "Direction introduction of genes into rats and expression of the genes," *Proc. Na'l. Acad. Sci. USA*, 83:9551–9555, 1986.

Brown et al., *Breast Cancer Res. Treat.*, 16:192(#191), 1990.

Bouck, N. "P53 and angiogenesis" Biochimica et Biophysica Acta 1287: 63–66 (1996).

Boussif et al., "A versatile vector for gene and oligonucleotide transfer into cells in culture and in vivo: Polyethylenimine," *Proc. Nat'l Acad. Sci. USA*, 92:7297–7301, 1995.

Cai et al., "Stable Expression of the Wild-Type p53 Gene in Human Lung Cancer Cells after Retrovirus-Mediated Gene Transfer," *Hum. Gene Ther.* 4:617–624, 1993.

Campbell et al., *J. Mol. Biol.*, 180:1–19, 1984.

Chang et al., "Foreign gene delivery and expression in hepatocytes using a hepatitis B virus vector," *Hepatology*, 14:124A, 1991.

Chen and Okayama, "High-efficiency transfection of mammalian cells by plasmid DNA," *Mol. Cell Biol.*, 7:2745–2752, 1987.

Coffin, "Retroviridae and their replication," In: Fields B N, Knipe D M, ed. Virology. New York: Raven Press, pp. 1437–1500, 1990.

Coupar et al., "A general method for the construction of recombinant vaccinia virus expressing multiple foreign genes," *Gene*, 68:1–10, 1988.

Dameron K M, Volpert O V, Tainsky M A and Bouck N. "Control of angiogenesis in fibroblasts by p53 regulation of thrombospondin-1" Science 265: 1582–1584 (1994).

Dubensky et al., "Direct transfection of viral and plasmid DNA into the liver or spleen of mice," *Proc. Nat'l Acad. Sci. USA*, 81:7529–7533, 1984.

Fechheimer et al., "Transfection of mammalian cells with plasmid DNA by scrape loading and sonication loading," *Proc. Nat'l Acad. Sci. USA*, 84:8463–8467, 1987.

Ferkol et al., "Regulation of the phosphoenolpyruvate carboxykinase/human factor IX gene introduced into the livers of adult rats by receptor-mediated gene transfer," *FASEB J.*, 7:101–1091, 1993.

Fraley et al., "Entrapment of a bacterial plasmid in phospholipid vesicles: Potential for gene transfer," *Proc. Nat'l Acad. Sci. USA*, 76:3348–3352, 1979.

Freshner, "Animal Cel Culture: A Practical Approach," Second Edition, Oxford/New York, IRL Press, Oxford University Press, 1992.

Friedmann, "Progress toward human gene therapy," *Science*, 244:1275–1281, 1989.

Gefter et al. *Somatic Cell Genet.* 3:231–236 (1977).

Ghosh and Bachhawat, "Targeting of liposomes to hepatocytes," In: Wu G, Wu C ed. Liver diseases, targeted diagnosis and therapy using specific receptors and ligands. New York: Marcel Dekker, pp. 87–104, 1991.

Gopal, "Gene transfer method for transient gene expression, stable transfection, and cotransfection of suspension cell cultures," *Mol. Cell Biol.*, 5:1188–1190, 1985.

Goyette et al, "Progression of colorectal cancer is associated with multiple tumor suppressor gene defects but inhibition of tumorigenicity is accomplished by correction of any single defect via chromosome transfer," *Mol. Cell Biol.*, 12(3): 1387–1395, 1992.

Graham et al., "Characteristics of a human cell line transformed by DNA from human adenovirus type 5", *J. Gen. Virol.*, 36:59–72, 1977.

Graham and Prevec, "Manipulation of Adenovirus Vectors," In: Murray, E. J ed. Methods in Molecular Biology, Vol. 7. Clifton, N.J.: The Humana Press Inc., pp 109–127.

Graham and van der Eb, "A new technique for the assay of infectivity of human adenovirus 5 DNA", *Virology*, 52:456–467, 1973.

Gruentzig et al., "Long term Follow up After PTCA: The Early Zurich Experience," *N. Engl. J. Med.*, 316:1127–1132, 1987.

Grunhaus and Horwitz, "Adenovirus as cloning vector," *Seminar in Virology*, 3:237–252, 1992.

Hannun and Bell, "The Sphingomyelin Cycle and the Second Messenger Function of Ceramide," *Jour. Of Biol. Chem.*, 299(5): 3125–3128, 1994.

Hannun and Bell, "Functions of Sphingolipids and Sphingolipid Breakdown Products in Cellular Regulation," *Science*, 243: 500–506, 1989.

Harland and Weintraub, "Translation of mammalian mRNA injected into Xenopus oocytes is specilically inhibited by antisense RNA," *J. Cell Biol*, 101:1094–1099, 1985.

Hermonat and Muzycska, "Use of adenoassociated virus as a mammalian DNA cloning vector: Transduction of neomycin resistance into mammalian tissue culture cells," *Proc. Nat'l Acac. Sci. USA*, 81:6466–6470, 1984.

Horwich, et al., "Synthesis of hepadnavirus particles that contain replication-defective duck hepatitis B virus genomes in cultured HuH7 cells," *J. Virol.*, 64:642–650, 1990.

Kaneda et al., "Increased expression of DNA cointroduced with nuclear protein in adult rat liver," *Scienc*, 243:375–378, 1989.

Kato et al., "Expressioin of hepatitis B virus surface antigen in adult rat liver," *J Biol. Chem.*, 266:3361–3364, 1991.

Klein et al., "High-velocity microprojectiles for delivering nucleic acids into living cells," *Nature*, 327:70–73, 1987.

Kohler & Milstein, *Eur. J. Immunol.*, 6:511–519, 1976.

Leimgruber et al., "Restenosis after Successful Coronary Angioplasty in Patients with Single Vessel Disease," *Circulation*, 73:710–717, 1986.

Mann et al., "Construction of a retrovirus packaging mutant and its use to produce helper-free defective retrovirus," *Cell*, 33:153–159, 1983.

Meyers, EPO 0273085

Mizrahi, *Process Biochem.*, (August):9–12, 1983.

Montenarh, "Biochemical, immunological, and functional aspects of the growth-suppressor/oncoprotein p53," *Crit. Rev. Oncogen*, 3:233–256, 1992.

Mukhopadhyay D, Tsickas L and Sukhatme V P. "Wild-type p53 and v-Src exert opposing influences on human vascular endothelial growth factor gene expression" *Cancer Research* 55: 6161–6165 (1995).

Nicolas and Rubenstein, "Retroviral vectors," In: Rodriguez RL, Denhardt DT, ed. Vectors: A survey of molecular cloning vectors and their uses. Stoneham: Butterworth, pp. 493–513, 1988.

Nicolau and Sene, "Liposome-mediated DNA transfer in eukaryotic cells," *Biochim. Biophys. Acta*, 721:185–190, 1982.

Nicolau et al., "Liposomes as carriers for in vivo gene transfer and expression," *Methods Enzymol.*, 149:1:;7–176, 1987.

Nobuyoshi et al., "Restenosis After Successful Percutaneous Transluminal Coronary Angioplasty; Serial Angiographic Follow-up of 220 Patients," *Jour. Am. Coll. Cardiol.*, 12:616–623, 1988.

Paskind et al., "Dependence of moloney murine leukemia virus production on cell growth," *Virology*, 67:242–248, 1975.

Perales et al., "Gene transfer in vivo: Sustained expression and regulation of genes introduced into the liver by receptor-targeted uptake," *Proc. Nat'l Acad. Sci.* 91:4086–4090, 1994.

Perrin et al., Buffers for pH and Metal Ion Control. New York: John Wiley & Sons, Inc.; p.51, 1974.

Phillips et al., *In: Large Scale Mammalian Cell Culture* (Feder, J. and Tolbert, W. R., eds.), Academic Press, Orlando, Fla., U.S.A., 1985.

Potter et al., "Enhancer-dependent expression of human k immunoglobulin genes introduced into mouse pre-B lymphocytes by electroporation," *Proc. Nat'l Acad. Sci. USA*, 81:7161–7165, 1984.

Ridgeway, "Mammalian. expression vectors," In. Rodriguez R L, Denhardt D T, ed. Vectors: A survey of molecular cloning vectors and their uses. Stoneham: Butterworth, pp. 167–492, 1988.

Rippe et al., "DNA-mediated gene transfer into adult rat hepatocytes in primary culture," *Mol. Cell Biol.*, 10:689–695, 1990.

Roth et al., "Gene replacement strategies for the prevention and therapy of cancer," *European Journal Cancer*, 30A:2032–2037, 1994.

Roux et al., "A versatile and potentially general approach to the targeting of specific cell types by retroviruises: Application to the infection of human cells by means of major histocompatibility complex class I and class II antigens by mouse ecotropic murine leukemia virus-derived viruses," *Proc. Nat'l Acad. Sci. USA*, 86:9079–9083, 1989.

Sambrook et al., Molecular Cloning: A Laboratory Manual, Cold Spring Harbor Press, Cold Spring Harbor, N.Y., 1989.

Serruys et al., "Incidence of Restenosis After Successful Coronary Angioplasty: A Time Related Phenomenon. A Quantitative Angiographic Study in 342 Consecutive Patients at 1, 2 and 3 Months," *Circulation*, 79:1374–1386, 1989.

Spandidos et al., "Onceogenes and onco-suppressor genes: their involvement in cancer," *Journal of Pathology*, 157 (1): 1–10, 1989.

Stratford-Perricaudet and Perricaudet, "Gene transfer into animals: the promise of adenovirus," p.51–61, *In: Human Gene Transfer*, Eds, O. Cohen-Haguenauer and M. Boiron, Editions John Libbey Eurotext, France, 1991.

Temin, "Retrovirus vectors for gene transfer: Efficient integration into and expression of exogenous DNA in vertebrate cell genome," In: Kucherlapati R, ed. Gene transfer. New York: Plenum Press, pp. 149–188, 1986.

Tooze, "Molecular biology of DNA Tumor viruses", 2nd ed. Cold Spring Harbor Laboratory, Cold Spring Harbor, N.Y., 1991.

Tur-Kaspa et al., "Use of electroporation to introduce biologically active foreign genes into primary rat lepatocytes," *Mol. Cell Biol.*, 6:716–718, 1986.

Van Meir E G, Polverini P J, Chazin VR, Huang H J, de Tribolet N and Cavenee W K. "Release of an in hibitor of angiogenesis upon induction of wild type p53 expression in glioblastoma cells" Nature Genetics 8: 171–176 (1994).

Verheij et al., "Requirement for ceramide-initiated SAPK/JNK signalling in stress-induced apoptosis," *Nature*, 380:75–79, 1996.

Volpert O V, Stellmach l and Bouck N. "The modulation of thrombospondin and other naturally occurring inhibitors of angiogenesis during tumor progression" *Breast Cancer Research and Treatment* 36:119–126 (1995).

Wagner et al, *Science*, 260:1510–1513, 1993.

Wong et al., "Appearance of b-lactamase activity in animal cells upon liposome mediated gene transfer," *Gene*, 10: 87–94, 1980.

Wu and Wu, *Adv. Drug Delivery Rev.*, 12:159–167, 1993.

Wu and Wu, "Evidence for targeted gene delivery to HepG2 hepatoma cells in vitro," *Biochemistry*, 27:887–892, 1988.

Wu and Wu, "Receptor-mediated in vitro gene transfections by a soluble DNA carrier system," *J. Biol. Chem.*, 262:4429–4432, 1987.

Yang et al., "In vivo and in vitro gene transfer to mammalian somatic cells by particle bombardment,". *Proc. Nat'l Acad. Sci. USA*, 87:9568–9572, 1990.

Zelenin et al., "High-velocity mechanical DNA transfer of the chloramphenicol acetyltransferase gene into rodent liver, kidney and mammary gland cells in organ explants and in vivo," *FEBS Lett.*, 280:94–96, 1991.

What is claimed is:

1. A method for preparing a composition comprising a factor having the following characteristics:
 a) resistant to protease;
 b) resistant to nuclease;
 c) resistant to heating at 100° C. for 10 minutes;
 d) resistant to freezing-thaw;
 e) resistant to lyophilization;
 f) pH stable; and
 g) has an apparent molecular weight of between about 0.5 and 1 kDa;
 h) has a biological activity of inhibiting the proliferation of a tumor cell;
wherein the method comprises the steps of:
 i) contacting a cell with a transcriptionally active expression vector which expresses a tumor suppressor gene;
 ii) culturing said cell in cell culture media under conditions where expression from said vector occurs; and
 iii) purifying said anti-proliferative factor by subjecting said culture media to size fractionation.

2. The method of claim 1, further comprising the step of removing said cell from said culture media.

3. The method of claim 2, further comprising physical separation of said factor from said cell culture media.

4. The method of claim 1, wherein said size fractionation eliminates molecules of greater than 300 kD.

5. The method of claim 1, wherein said size fractionation eliminates molecules of greater than about 3 kD.

6. The method of claim 2, further comprising treating said cell culture media with a protease or a nuclease.

7. The method of claim 2, further comprising heating said cell culture media.

8. The method of claim 1, wherein said cell is a tumor cell.

9. The method of claim 1, wherein said expression vector is a viral or plasmid vector.

10. The method of claim 9, wherein said vector is an adenovirus, retrovirus, adeno-associated virus, or a vaccinia virus.

11. The method of claim 9, wherein said vector comprises a promoter, a gene and a poly-adenylation signal.

12. The method of claim 1, wherein said tumor suppressor gene encodes wild-type p53.

13. The method of claim 11, wherein said gene encodes β-galactosidase.

14. The method of claim 2, wherein said removing is accomplished by centrifugation.

15. The method of claim 1, wherein the cell is cultured for about 24, about 48, or about 72 hours.

* * * * *

UNITED STATES PATENT AND TRADEMARK OFFICE
CERTIFICATE OF CORRECTION

PATENT NO. : 6,133,416  
DATED : October 17, 2000  
INVENTOR(S) : Deborah R. Wilson, Mary A. Lapadat-Tapolsky, Therese M. Timmons, Julia A. Lee, Brian D. Almond and Jack A. Roth It is certified that error appears in the above-identified patent and that said Letters Patent is hereby corrected as shown below:

<u>Title page,</u> under "Inventors:", please delete, "Mary Lapadat-Tapolsky", and insert -- Mary A. Lapadat-Tapolsky --.

Signed and Sealed this

Eighteenth Day of September, 2001

Attest:

*Nicholas P. Godici*

NICHOLAS P. GODICI  
*Attesting Officer*  *Acting Director of the United States Patent and Trademark Office*